US009657348B2

(12) United States Patent
Bengtsson

(10) Patent No.: US 9,657,348 B2
(45) Date of Patent: May 23, 2017

(54) METHOD OF SCREENING COMPOUNDS FOR THE TREATMENT OF DIABETES

(71) Applicant: ATROGI AB, Stockholm (SE)

(72) Inventor: Tore Bengtsson, Vaxholm (SE)

(73) Assignee: ATROGI AB, Stockholm (SE)

( * ) Notice: Subject to any disclaimer, the term of this patent is extended or adjusted under 35 U.S.C. 154(b) by 0 days.

(21) Appl. No.: 14/759,747

(22) PCT Filed: Jan. 13, 2014

(86) PCT No.: PCT/EP2014/050458
§ 371 (c)(1),
(2) Date: Jul. 8, 2015

(87) PCT Pub. No.: WO2014/108531
PCT Pub. Date: Jul. 17, 2014

(65) Prior Publication Data
US 2015/0344958 A1 Dec. 3, 2015

Related U.S. Application Data

(60) Provisional application No. 61/751,894, filed on Jan. 13, 2013.

(51) Int. Cl.
| | | |
|---|---|---|
| *C12Q 1/68* | (2006.01) |
| *G01N 33/68* | (2006.01) |
| *G01N 33/50* | (2006.01) |
| *A61K 31/137* | (2006.01) |
| *C07K 14/72* | (2006.01) |
| *C12Q 1/48* | (2006.01) |
| *C07K 14/70* | (2006.01) |
| *C12N 9/12* | (2006.01) |
| *G01N 33/566* | (2006.01) |
| *C07K 14/705* | (2006.01) |

(52) U.S. Cl.
CPC .......... *C12Q 1/6883* (2013.01); *A61K 31/137* (2013.01); *C07K 14/70571* (2013.01); *C07K 14/723* (2013.01); *C12N 9/1205* (2013.01); *C12Q 1/485* (2013.01); *G01N 33/502* (2013.01); *G01N 33/566* (2013.01); *G01N 33/6872* (2013.01); *C12Q 2600/136* (2013.01); *C12Q 2600/158* (2013.01); *G01N 2333/4703* (2013.01); *G01N 2333/726* (2013.01); *G01N 2500/00* (2013.01); *G01N 2500/10* (2013.01); *G01N 2800/04* (2013.01); *G01N 2800/042* (2013.01)

(58) Field of Classification Search
CPC .... C12Q 1/485; C12Q 1/6883; A61K 31/137; G01N 33/502; G01N 33/566; G01N 33/6872; C07K 14/70571; C07K 14/723; C12N 9/1205
See application file for complete search history.

(56) References Cited

U.S. PATENT DOCUMENTS

| | | |
|---|---|---|
| 2010/0173928 A1 | 7/2010 | Sabatini et al. |
| 2016/0003803 A1 | 1/2016 | Bengtsson |

FOREIGN PATENT DOCUMENTS

| | | |
|---|---|---|
| EP | 2426202 A1 | 3/2012 |
| WO | 99/35279 A1 | 7/1999 |
| WO | 99/43326 A1 | 9/1999 |
| WO | 2004/004451 A1 | 1/2004 |
| WO | 2005/013666 A2 | 2/2005 |
| WO | 2005/114195 A1 | 12/2005 |
| WO | 2009/156413 A1 | 12/2009 |

OTHER PUBLICATIONS

Ahren et al., Cell Tissue Res., 1981, 216, 15-30.
Alessi et al., Curr. Biol., 1997, 7, Z61-269.
Arch et ai., Int. J. Obes., 1996, 20, 191-199.
Barnes et al., J. Celi Sci., 2002, 115, 2433-2442.
Brown et al., Nature, 7 994, 369, 756-758.
Cannon et al., Physiol. Rev., 2004, 84, 277-359.
Carayannopoulos et al., Proc. Natl. Acad. Sci. U.S.A., 2000, 97, 7313-7318.
Chandler et al., Cancer, 2003, 97, 2035-2042.
Chernogubova et aL, Endocrinology, 2004, 145, 269-280.
Chernogubova et al., Endocrinology, 2005, 146, 2271-2284.
Copp et aL, Cancer Res., 2009, 69, 1821-1827.
Dallner et al., Endocrinology, 2006, 147, 5730-5739.
DeFronzo et al., J. Clin. Invest., 1981, 68, 468-1474.
Dehvari et al., Br. J. Pharmacol., 2012, 165, 1442-1456.
Drake et al., Circ. Res., 2006, 99, 570-582.
Exton. Diabetes Metab. Rev., 1987, 3, 163-183.
Feldman et aL, PLoS Biol., 2009, 7, 371-383.
Garcia-Martinez et al., Biochem. J., 2009, 421, 29-42.
Gawlik et aL, Mol. Membr. Biol., 2008, 25, 224-235.
Gilman et al., Annu. Rev. Biochem., 1987, 56, 615-649.
Green et al., J. Biol. Chem., 2008, 283, 27653-27667.
Gusovsky, Curr. Protoc. Neurosci., 2001, 7:7:7.12.1-7.12.11.
Harrison of al., Proc. NatL Acad. Sci. U.S.A., 1991, 88, 7839-7843.
Harrison et al., J. Biol. Chem., 1992, 267, 3783-3788.
Hawkins et al., Biochem. Soc. Trans., 2006, 34, 647-662.
Hebert et al., J. Biol. Chem., 1986, 261, 10093-10099.
Hresko et al., J. Biol. Chem., 2005, 280, 40406-40416.
Huang et al., Methods Mol. Biol., 2012, 821, 75-86.

(Continued)

*Primary Examiner* — Robert Landsman
(74) *Attorney, Agent, or Firm* — McCarter & English, LLP; Steven G. Davis; Mei Bai

(57) ABSTRACT

A method of screening for a candidate compound for the treatment of a condition involving dysregulation of metabolism in a mammal, by bringing a compound into contact with cells that express a GPCR and that further express a GRK, determining whether the contacting causes a response of the GRK in cells brought into contact with the compound, determining whether the contacting causes a response of a classical secondary messenger in cells brought into contact with the compound; and identifying the candidate compound based on the determined GRK response and response of a classical secondary messenger in the cells. A kit for use in the method. A compound for use in the treatment of a condition involving dysregulation of metabolism in a mammal and a method of treatment of such a condition.

11 Claims, 16 Drawing Sheets

(56) References Cited

OTHER PUBLICATIONS

Huang et al., Cell Metab., 2007, 5, 237-252.
Hutchinson et al., Endocrinology, 2005, 146, 901-912.
Hutchinson et al., Diabetes, 2006, 55, 682-690.
Hutchinson et al., Naunyn-Schmiedeberg's Arch. Pharmacol, 2006, 373, 158-168.
Inokuma et al, Diabetes, 2005, 54, 1385-1391.
Jones et al., Exp. Physiol., 2003, 88, 277-284.
Kleiman et al., Biochem. Biophys. Res. Commun., 2009, 388, 554-559.
Koshy et al., J. Vis. Exp., 2010, 45, 10.3791/2429.
Kumar et aL, Diabetes, 2010, 59, 1397-1406.
Lacey et al., Br. J. Pharmacol., 1991, 103, 1824-1828.
Lamming et al., Cell Metab., 2013, 18, 465-469.
Laplante et al., Cell, 2012, 149, 274-293.
Lawrence et al., Proc. Natl. Acad. Sci. U.S.A., 1992, 89, 3493-3497.
Liggett et aL, Am. J. Physiol., 1988, 254, 795-8.
Liu et al., Am. J. PhysioL, 1994, 266, 914-20.
Liu et al., Br. J. Pharmacol., 1996, 117, 1355-1361.
Macaulay et al., Mol. Cell. Biochem., 1994, 141, 27-33.
Macheda et al., J. Cell. Physio., 2005, 202, 654-662.
Marette et al., Am. J. Physiol., 1989, 257, 714-21.
Murata et al., AIDS, 2002, 16, 859-863.
Nave et ai., Biochem. J., 1999, 344, 427-431.
Nedergaard of al., Cell Metab., 2011, 13, 238-240.
Nedergaard et al.., Ann. N. Y. Acad. Sci., 2010, 1212, 20-36.
Nedergaard et al., Am. J. Physiol-Endoc. M., 2007, 293, 444-52.
Nedergaard et al., Biochim. Biophys. Acta, 2005, 1740, 293-304.
Nevzorova et al., Br. J. Pharmacol., 2002, 137, 9-18.
Nevzorova et al., Br. J. Pharmacol., 2006, 147, 446-454.
Ngala et al., Br. J. Pharmacol., 2008, 155, 395-406.
Ngala et al., Br. J. Pharmacol., 2009, 158, 1676-1682.
Nobles et al., Sci. Signal., 2011, 4, RA51.
Nugent et. al. Mol. Endocrinol., 2001, 15, 1729-1738.
Palmada et al., Diabetes, 2006, 55, 421-427.
Phung et al., Cancer Cell, 2006, 10, 159-170.
Ploug et al., Am. J. Physiol., 1987, 253, 12-20.
Polak et al., Cell Metab., 2008, 8, 399-410.
Reinicke et al., J. Cell. Biochem., 2012, 113, 553-562.
Rodnick et al., Diabetes Care, 1992, 15, 1679-1689.
Rowland et al., Traffic, 2011, 12, 672-681.
Santulli et al., Immun Ageing, 2013, 10:10.
Sarabia et al., Biochem. Cell Biol., 1990, 68, 536-542.
Sarbassov et al., Curr. Biol., 2004, 14, 1296-1302.
Sekulic et al., Cancer Res., 2000, 60, 3504-3513.
Shah et al., Int. J. Mol. Sci., 2012, 13, 12629-12655.
Shenoy et al., IJPSR, 2011, 2, 2490-2500.
Shibata et al., Am. J. Physiol., 1989, 257, 96-101.
Shimizu et al., Am. J. Physiol., 1991, 261, 301-304.
Simpson et al., Am. J. Physiol—Endoc. M., 2008, 295, 242-253.
Sobel et al., J. Bacteriol., 1973, 116, 271-278.
Stanford et al., J. Clin. Invest., 2013, 123, 215-223.
Taha et al., The J. Biol. Chem., 1995, 270, 24678-24681.
Tavema et al., Biochim. Biophys. Acts., 1973, 323, 207-219.
Thong et al., Physiology, 2005, 20, 271-284.
Vardanega-Peicher et al., Braz. J. Med. Biol. Res., 2000, 33, 8-5-813.
Violin et al., J. Biol. Chem., 2006, 281, 20577-20588.
Watson-Wright, et al., Muscle Nerve, 1989, 9, 416-422.
Yamamoto et al., Diabetologia, 2007, 50, 158-167.
Zeng et al., Blood, 2007, 109, 3509-3512.
Zierath, Acta. Physiol. Scand. Suppl., 1995, 626, 1-96.
Zinzalla et al., Cell, 2011, 144, 757-768.
International Search Report and Written Opinion issued in International Application No. PCT/EP2014/050458, mailed Mar. 14, 2014.

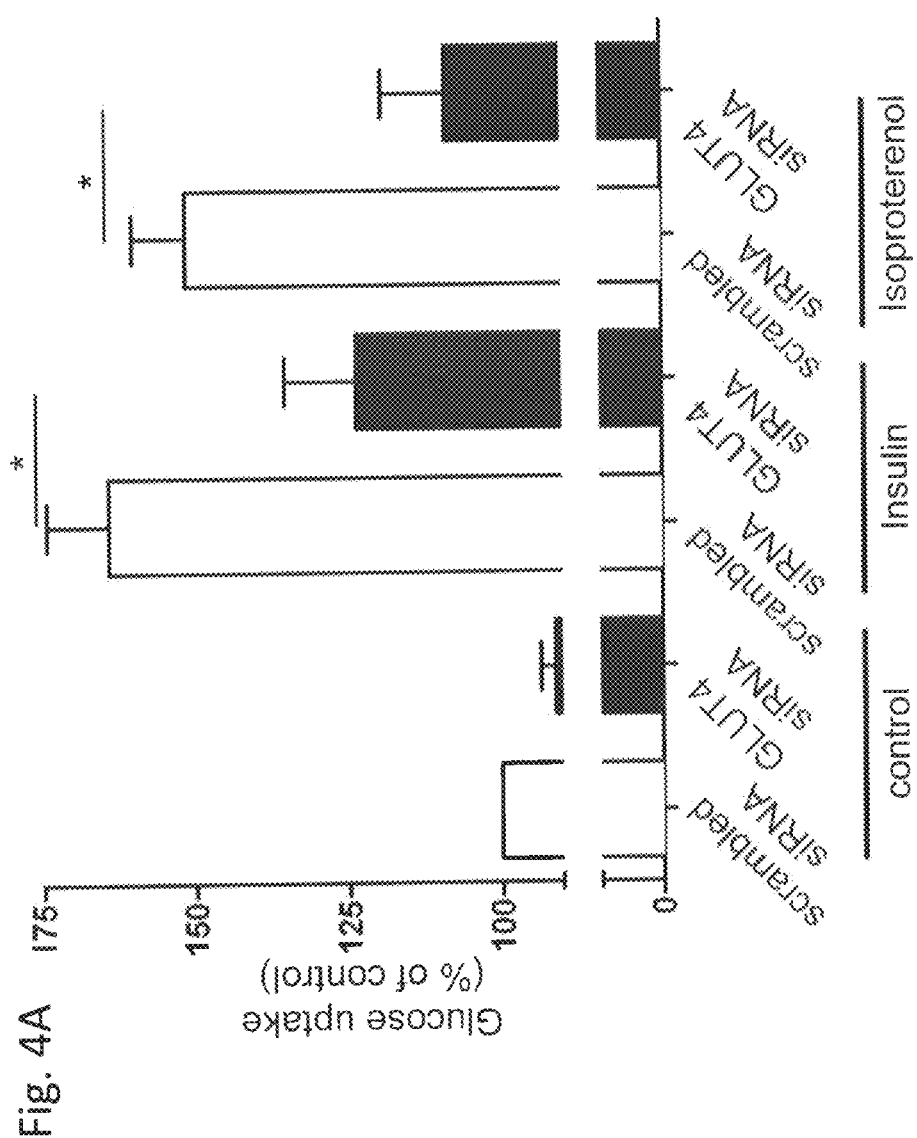
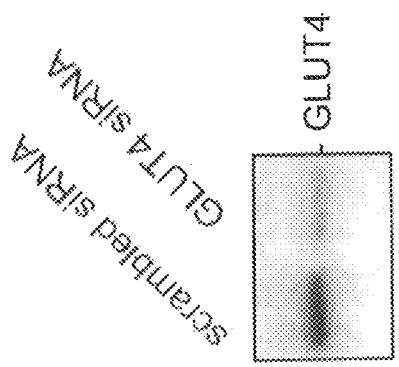

METHOD OF SCREENING COMPOUNDS FOR THE TREATMENT OF DIABETES

CROSS-REFERENCE TO RELATED APPLICATIONS

This application is a 35 U.S.C. §371 national stage filing of International Application No. PCT/EP2014/050458, filed on Jan. 13, 2014, which claims the benefit of U.S. Provisional Application No. 61/751,894, filed on Jan. 13, 2013. Each of the foregoing applications is incorporated herein by reference in its entirety.

FIELD OF THE INVENTION

The present invention relates to a screening method, in particular to a method of screening for a compound useful for the treatment of a condition involving a dysregulation metabolism such as glucose homeostasis or glucose uptake in a mammal in a mammal, as well as to a kit for use in such a method. The invention also relates to a compound for use in such treatment, and to a method of treatment of such a condition.

BACKGROUND OF THE INVENTION

Following a meal, increased blood glucose levels stimulate insulin release from the pancreas to act throughout the body to lower blood glucose levels. Important sites of action of insulin on glucose metabolism include facilitation of glucose uptake into skeletal muscle and adipocytes, and an increase of glycogen storage in the liver. Skeletal muscle and adipocytes is responsible for insulin-mediated glucose uptake and utilization in the fed state, making them very important site for glucose metabolism.

Diabetes comprises two distinct diseases, type 1 (or insulin-dependent diabetes) and type 2 (insulin-independent diabetes), both of which involve the malfunction of glucose homeostasis. Type 2 diabetes affects more than 350 million people in the world and the number is rising rapidly. Complications of diabetes include severe cardiovascular problems, kidney failure, peripheral neuropathy, blindness and even loss of limbs and death in the later stages of the disease. Type 2 diabetes is characterized by insulin resistance in skeletal muscle and adipose tissue (fat), and at present there is no definitive treatment. Most treatments used today are focused treating dysfunctional insulin signaling or inhibiting glucose output from the liver and many of those treatments have several drawbacks and side effects. There is thus a great interest in identifying novel insulin-independent ways to treat different form of metabolic orders connected with dysregulation of glucose uptake such as type 2 diabetes.

In type 2 diabetes the insulin-signaling pathway is blunted in peripheral tissues such as fat and skeletal muscle. Methods for treating type 2 diabetes typically include lifestyle changes, as well as the administration of insulin or oral medications to help the body with the glucose homeostasis. People with type 2 diabetes in the later stages of the disease develop "beta-cell failure" or the inability of the pancreas to release insulin in response to high blood glucose levels. In the later stages of the disease patients often require insulin injections, in combination with oral medications, to manage their diabetes. In type 2 diabetes the insulin-signaling pathway is blunted in peripheral tissues. Furthermore, most common drugs have side effects including the said down-regulation or desensitization of the insulin pathway and/or the promotion of fat incorporation in fat, liver and skeletal muscle, as well as increased stimulation of proliferation of certain cells and a higher risk of promoting cancer. There is thus a great interest in identifying novel ways to treat metabolic diseases including type 2 diabetes that do not include these said side-effects.

The molecular understanding of the signaling pathway below the insulin receptor has been a very hard problem to solve and have been occupying a great number of researchers since the discovery of insulin. In short, control of glucose uptake by insulin involves activation of the insulin receptor (IR), insulin receptor substrate (IRS), phosphoinositide 3-kinase (PI3K) and thus stimulation of phosphatidylinositol (3,4,5)-triphosphate (PIP3), mammalian target of rapamycin also called mechanistic target of rapamycin (mTOR), Akt/PKB (Akt) and TBC1D4 (AS160), leading to translocation of glucose transporter 4 (GLUT4). Akt activation is considered necessary for GLUT4 translocation.

It should be noted that skeletal muscles make up a major part of mammals and have a vital role in the regulation of systemic glucose metabolism, being responsible for up to 85% of whole-body glucose disposal (DeFronzo et al. 1981). Glucose uptake in skeletal muscles is regulated by several intra- and extracellular signals. The hormone insulin is the most well studied of the signals but other signals also exist. For example, AMP activated kinase, AMPK, functions as an energy sensor in the cell, which can increase glucose uptake and fatty acid oxidation. Also muscle contraction in itself can cause increased glucose uptake. Due to the great influence skeletal muscles have on glucose homeostasis it likely that further mechanisms exists. In the light of the increases prevalence of type II diabetes, it is of great interest to find and characterize novel insulin-independent mechanisms to increase glucose uptake in muscle cells.

Insulin and catecholamines are released in the body in response to quite different stimuli. Whereas insulin is released in response to the rise in blood sugar levels after a meal, epinephrine and norepinephrine are released due to various internal and external stimuli, such as exercise, emotions and stress but also homeostatic tissue regulation. Insulin is an anabolic hormone that stimulates many processes involved in growth including glucose uptake, glycogen and triglyceride formation whereas catecholamines are mainly catabolic. Although insulin and catecholamines normally have antagonistic effects, we have shown previously that they have similar actions in skeletal muscle on glucose uptake (Nevzorova et al. 2002). It is likely that catecholamines stimulate glucose uptake via adrenergic receptors (Nevzorova et al. 2006, Hutchinson, Bengtsson 2005) which are prototypical models for G protein-coupled receptors (GPCRs) and their signaling (Santulli, Iaccarino 2013, Drake, Shenoy & Lefkowitz 2006) to supply muscle cells with an energy substrate. Thus it is likely that in mammals, including humans, that GPCRs and insulin systems can work independently to provide for the energy need of skeletal muscle during different situations. Since insulin stimulate many anabolic processes including a number of unwanted side effects it would be beneficial to be able to stimulate glucose uptake through GPCRs that does not include many of the unwanted processes in the insulin signaling pathway.

It is well known in the art that adrenergic receptors are prototypical models for the study of G protein-coupled receptors (GPCRs) and their signaling (Santulli, Iaccarino 2013, Drake, Shenoy & Lefkowitz 2006). There are three different classes of ARs, with distinct expression pattern and pharmacological profiles: α1-, α2- and β-ARs. The α1-ARs comprise the α1A, α1B and α1D while α2-ARs are divided into α2A, α2B and α2C. The β-ARs are also divided into the subtypes β1, β2, and β3, of which β2-AR is the major isoform in skeletal muscle cells (Watson-Wright, Wilkinson 1986, Liggett, Shah & Cryer 1988). Adrenergic receptors are G protein coupled and signal through classical secondary messengers such as cAMP and phospholipase C and are thus suited as prototypical models for most classes of GPCRs. GPCRs are expressed in various tissues and many effects occurring downstream of GPCRs in skeletal muscles has been attributed to classical secondary messenger signaling, but there are also atypical events downstream of GPCRs dependent on a protein family called G protein-coupled receptor kinases (GRKs), and these are kinases which can phosphorylate the intracellular loops as well as the c-terminal tail of the receptor when it is activated. The different GRK isoforms give a distinct phosphorylation pattern, thus directing the further signal. This can be desensitization of the signal, internalization of the receptors and recruitment of β-arrestins. GRKs phosphorylate GPCRs domains after the GPCR has been activated resulting in receptor desensitization and internalization. GRKs also regulate GPCR trafficking in a phosphorylation-independent way via direct protein-protein interaction. In short GRKs phosphorylate serine and threonine residues on the GPCR in the intracellular domains which act as a docking site for proteins for example arrestins that are involved in desensitization of the GPCRs but as mentioned GRKs also regulate cellular responses independent on their kinase activity. Emerging evidence suggests that in particular GRK2 interacts with a diverse number of non-GPCR substrates (Evron, Daigle & Caron 2012a) modulating multiple cellular responses in various physiological contexts.

It has have previously been shown that GPCR and GRKs can increase glucose uptake in Chinese hamster ovary (CHO) cells (Dehvari et al. 2011) but this cell-line has little or no relevance to murine or human cells involved in glucose homeostasis in vivo. It has thus been unclear if GRKs can stimulate glucose uptake in relevant cells for glucose homeostasis and, if so, through which mechanisms.

GPCR stimulated glucose uptake has been attributed to classical secondary messenger stimulation such as increase in cAMP levels, phospholipase C (PLC) activity and calcium levels (Gilman 1987). The increase of these classical secondary messengers has many effects in different tissues. For example, it increases heart rate, regulates blood flow, airflow in lungs and increases release of glucose from the liver, which all can be detrimental or be considered unwanted side effects if stimulation of GPCRs should be considered as a diabetes treatment. Adverse effects of GPCR agonists are for example tachycardia, palpitation, tremor, sweats, agitation and increased glucose levels in the blood (glucose output from the liver). All these effects can be attributed to GPCR stimulated elevation of classical secondary messengers in various tissues. It would thus be beneficial to be able to activate GPCR without activating these classical secondary messengers to increase glucose uptake in peripheral tissues without stimulating the unwanted side effects.

Glucose uptake is mainly stimulated via facilitative glucose transporters (GLUT) that mediate glucose uptake into most cells. GLUTs are transporter proteins that mediate transport of glucose and/or fructose over the plasma membrane down the concentration gradient. There are fourteen known members of the GLUT family, named GLUT1-14, divided into three classes (Class I, Class II and Class III) dependent on their substrate specificity and tissue expression. GLUT1 and GLUT4 are the most intensively studied isoforms and, together with GLUT2 and GLUT3, belong to Class I which mainly transports glucose (in contrast to Class II that also transports fructose). GLUT1 is ubiquitously expressed and is responsible for basal glucose transport. GLUT4 is only expressed in peripheral tissues such as skeletal muscle, cardiac muscle and adipose tissues. GLUT4 has also been reported to be expressed in e.g. brain, kidney, and liver. GLUT4 is the major isoform involved in insulin stimulated glucose uptake. To treat a condition involving a dysregulation of glucose homeostasis or glucose uptake in a mammal, it is of paramount importance to activate certain GLUTs. For example for diseases such as type 2 diabetes it is vital to activate GLUT4 translocation to the plasma membrane and thus glucose uptake. Regulation of GLUT1 translocation or intrinsic activity has been suggested to occur in several tissues including erythrocytes depending on ATP-levels (Hebert, Carruthers 1986). It has also been indicated in HEK-cells (Palmada et al. 2006), 3T3-L1 (Harrison et al. 1992) and clone-9 cells (Barnes et al. 2002). Impaired GLUT translocation, of in particular GLUT8, has been reported as involved in both male and female infertility (Gawlik et al. 2008, Carayannopoulos et al. 2000). The mechanism whereby insulin signaling increases glucose uptake is mainly via GLUT4-translocation from intracellular storage to the plasma membrane (Rodnick et al. 1992). After longer insulin stimulation also GLUT1-content is increased due to increased transcription (Taha et al. 1995). Glucose uptake in type 2 diabetes is associated with defects in PI3K activity, insulin receptor tyrosine, IRS and Akt phosphorylation, resulting in impairment of GLUT4 translocation to the plasma membrane. Impaired GLUT translocation also plays a role in muscle wasting. Furthermore, GLUT translocation plays a role in feeding behavior. Mice lacking GLUT4 develop problems with lipid and glucose homeostasis leading to changes in feeding behavior. Decreased concentrations of GLUT1 and GLUT3 have also been shown in the brains of patients with Alzheimer's disease (Simpson et al. 2008). Also in a review article of Shah K, et al. (Shah, Desilva & Abbruscato 2012) the role of glucose transporters in brain disease, diabetes and Alzheimer's disease is discussed.

SUMMARY OF THE INVENTION

It has been surprisingly found that GPRCs can stimulate glucose uptake and that GRK is involved in this process. Furthermore, it has been surprisingly found that GPCRs can activate GRK without activating classical secondary messengers. Moreover, it has been found that activation of GRK in a cell may lead to translocation of GLUT, leading to an enhanced glucose uptake in the cell. In view of these findings, it is contemplated that drugs that stimulate GRKs can be used in treating metabolic disorders related to dysregulation of hexose transport, in particular glucose transport, including insulin resistance or hyperglycemia, type 2 diabetes, inadequate glucose tolerance, obesity, polycystic ovary syndrome (PCOS), hypertension and the metabolic syndrome Based on the above findings, therefore, a first aspect is a method of screening for a candidate compound for the treatment of a condition involving dysregulation of metabolism in a mammal, said method comprising:

bringing a compound into contact with cells that express a GPCR and that further express a GRK, determining whether the contacting causes a response of the GRK in cells brought into contact with the compound, determining whether the contacting causes a response of a classical secondary messenger in cells brought into contact with the compound; and identifying the candidate compound based on the determined GRK response and response of a classical secondary messenger in the cells.

For example, the candidate compound may be identified by comparing the determined GRK response and response of a classical secondary messenger, with response of the GRK and response of the classical secondary messenger determined in cells that have not been brought into contact with the compound. Basically, a compound is identified as a candidate compound if it causes a significant response of a GRK, but does not cause a significant response of a classical secondary messenger in the cells.

The classical secondary messenger e.g. may be diacylglycerol (DAG), phosphatidylinositols (PI), cyclic adenosine monophosphate (cAMP), cyclic guanosine monophosphate (cGMP), inositol trisphosphate (IP3), calcium ion ($Ca^{2+}$), and nitric oxide (NO), carbon monoxide (CO) and hydrogen sulphide ($H_2S$).

The GPCR e.g. may be an adrenergic receptor, such as a beta adrenergic receptor, or an alpha adrenergic receptor.

Some embodiments comprise bringing the compound into contact with cells that express a GPCR and that further express a GRK and a GLUT, e.g. a GLUT selected from GLUT1, GLUT3 and GLUT4, in particular GLUT4. In these embodiments, a response of the GLUT in cells brought into contact with the compound may be determined, e.g. by detecting the presence of a GLUT in the cell membrane of the cells, or by measuring uptake of a hexose, e.g. glucose, in cells brought into contact with the compound.

Thus, in some embodiments, the candidate compound is further identified by comparing a GLUT response determined in cells brought into contact with the screened compound, with a GLUT response determined in cells that have not been brought into contact with the compound.

The cells used in the screening method of the invention preferably are mammalian cells, e.g. cells selected from skeletal muscle cells, heart cells, adipocytes, such as brown fat cells and white fat cells, beta cells, brain cells, liver cells, reproductive cells and cells involved in reproduction, and mammary cells. In particular, the cells may be selected from muscle cells and adipocytes, e.g. muscle cells.

The condition involving a dysregulation of metabolism in a mammal for example is a condition involving a dysregulation of glucose homeostasis or glucose uptake.

In some embodiments, the condition is selected from Alzheimer's disease, blindness, cardiovascular disease, central nervous system diseases, diabetes, dyslipidemia, hypertension, kidney disease, macular degeneration, metabolic disorders, neurodegenerative diseases, obesity, peripheral neuropathy, reduced fertility and infertility, retinopathy, stroke, and vascular disease. For example, the condition may be diabetes.

Another aspect is a kit for use in a method of screening for a candidate compound for the treatment of a condition involving a dysregulation of metabolism in a mammal, said kit comprising cells capable of expressing a GPCR, which cells are further capable of expressing a GRK, together with instructions for use of the kit.

In some embodiments, the GPCR is an adrenergic receptor, e.g. a beta adrenergic receptor. In some other embodiments, the GPCR is an alpha adrenergic receptor.

In some embodiments, the kit comprises cells capable of expressing a GPCR, which cells are further capable of expressing a GRK and a GLUT, e.g. a GLUT selected from GLUT1, GLUT3 and GLUT4, in particular GLUT4.

The kit preferably comprises mammalian cells, e.g. cells selected from skeletal muscle cells, heart cells, adipocytes, such as brown fat cells and white fat cells, beta cells, brain cells, liver cells, reproductive cells and cells involved in reproduction, and mammary cells. In particular, the cells may be selected from muscle cells and adipocytes, e.g. muscle cells.

One aspect is a compound for use in a method of treatment or prevention of a condition involving a dysregulation of metabolism in a mammal, by administering to a mammal in need of such treatment or prevention a therapeutically effective amount of a compound which activates a GRK in at least some cells of the mammal, but which compound does not cause a response of a classical secondary messenger in cells of the mammal.

A further aspect is a method of treatment or prevention of a condition involving a dysregulation of metabolism in a mammal, by administering, to a mammal in need of such treatment or prevention, a therapeutically effective amount of a compound which activates a GRK in at least some cells of the mammal, but which compound does not cause a response of a classical secondary messenger in cells of the mammal.

BRIEF DESCRIPTION OF THE DRAWINGS

FIGS. 1A-1C illustrate that activating a prototypical GPCR may lead to increased (i.e. stimulated) glucose uptake in skeletal muscle cells.

FIGS. 2A-2C illustrate that activating a prototypical GPCR may lead to increased glucose uptake and that this uptake is mediated by glucose transporters, GLUTs.

FIGS. 3A and 3B illustrate that, whether stimulated by insulin or agonists of prototypical GPCR, glucose uptake occurs through a similar mechanism, which mechanism follows classical Michaelis-Menten parameters.

FIGS. 4A and 4B are (4A) a bar chart showing glucose uptake (% of control) in L6 myotubes brought into contact with insulin, isoproterenol or, as a control, vehicle only, after transfection with scrambled siRNA or GLUT4 siRNA; and (4B) a western blot of GLUT4 and the protein Akt, from L6 myotubes treated with scrambled siRNA or GLUT4 siRNA. FIGS. 4A and 4B illustrate that prototypical GPCRs stimulated glucose uptake in skeletal muscle is dependent on GLUT4.

FIGS. 5A-5E illustrate that transcription and translation are not involved in prototypical GPCR stimulated glucose uptake.

FIGS. 6A and 6B illustrate that prototypical GPCRs lead to translocation of GLUT4 to the plasma membrane in L6 skeletal muscle cells as well as in human skeletal muscle cells.

FIG. 7 illustrates that downregulation of GRK with siRNA inhibits glucose uptake stimulated by agonists for prototypical GPCRs, but does not inhibit glucose uptake stimulated by insulin.

FIG. 8 illustrates that also in other cells than muscle cells downregulation of GRK with siRNA inhibits prototypical GPCR stimulated glucose uptake, but does not inhibit glucose uptake stimulated by insulin.

FIGS. 9A and 9B illustrate that downregulation of GRK with siRNA inhibits prototypical GPCR stimulated glucose uptake that is not dependent on the classical secondary messenger cAMP.

DETAILED DESCRIPTION

Figure 1A:
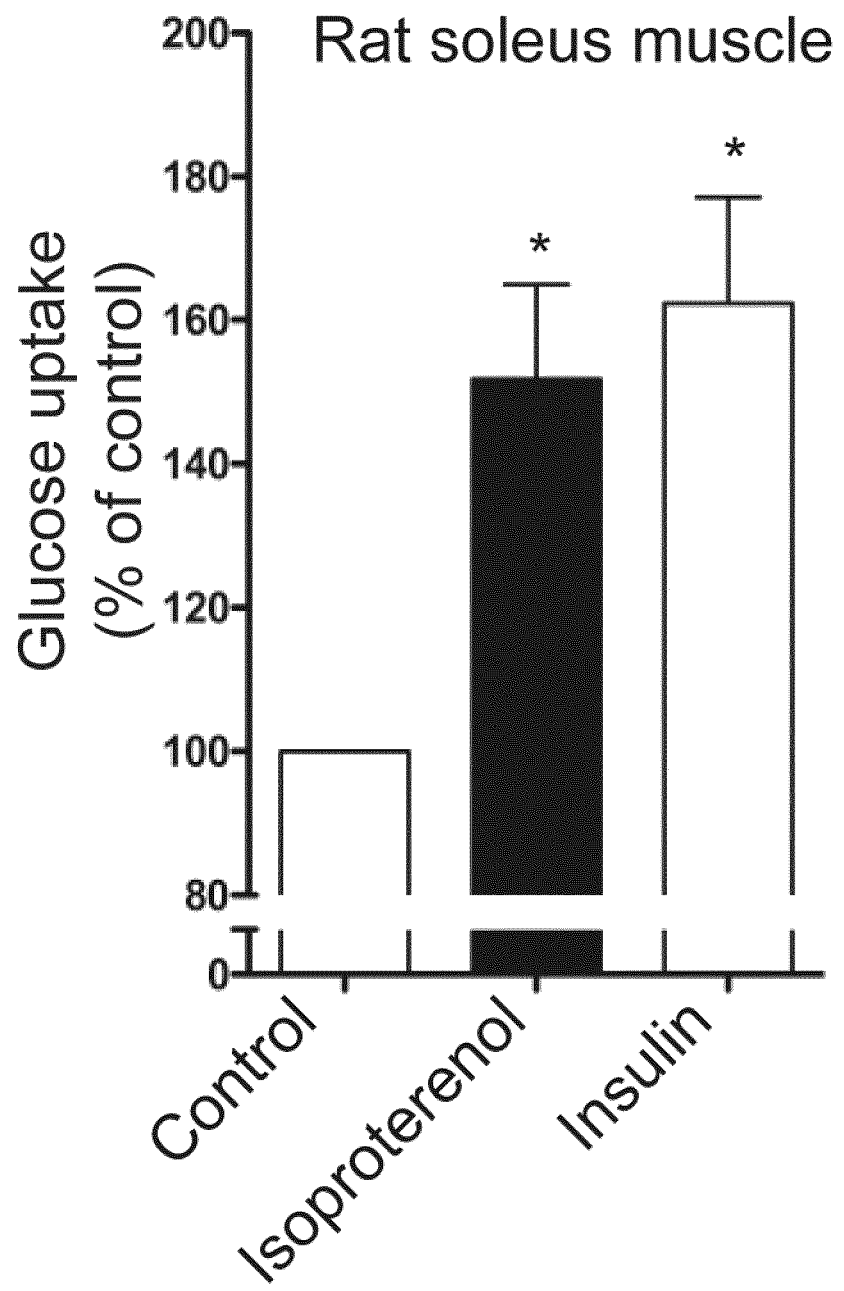
FIGS. 1A-1C are bar charts showing glucose uptake (% of control) in (1A) soleus muscle from rat, (1B) L6 myotubes, and (1C) human skeletal muscle cells, respectively, brought into contact with isoproterenol, insulin or, as a control, vehicle only.

By GPCR ligand is meant any molecule capable of binding GPCRs. The GPCR ligand can be selected from known or unknown GPCR ligands and agonists. Ligand denotes here any molecule binding to the receptor.

A compound that either binds GPCR directly or acts by stabilizing the GPCR is referred to herein as a ligand for GPCR.

By a condition involving a dysregulation of glucose homeostasis or glucose uptake in a mammal is meant a condition, disease or disorder induced by, regulated by, or associated with a dysregulation of glucose homeostasis or glucose uptake in a mammal. Such a condition may be e.g. Alzheimer's disease, blindness, cardiovascular disease, central nervous system diseases, diabetes, dyslipidemia, hypertension, kidney disease, macular degeneration, metabolic disorders, neurodegenerative diseases, obesity, peripheral neuropathy, reduced fertility and infertility, retinopathy, stroke, vascular disease, etc.

It should be realized that even when identified as a "candidate compound for the treatment of a condition involving dysregulation of metabolism in a mammal", the compound may have to pass various other tests, e.g. pharmacological, clinical and toxicological tests so on, before being able to be used as a drug. Thus, the expression "candidate compound for the treatment of a condition involving dysregulation of metabolism in a mammal" should not be generally construed as a statement that the method permits to positively identify a compound for use in such a treatment, but rather should be understood as an indication that the method permits to identify a compound that may have a usefulness in such treatment.

The word "cell" as used herein, generally refers to a plurality of cells, and not to one single cell, unless the contrary is specified or apparent from the context.

By "GLUT" is meant any of the 14 mammalian glucose transporter proteins, GLUT1-14. Reference to "GLUT" in singular does not mean one GLUT only, unless apparent from the context or otherwise specified, but should be construes as reference to a plurality of mammalian glucose transporter proteins. Preferably the GLUT is a GLUT belonging to class I, in particular GLUT1, GLUT3 or GLUT4, preferably GLUT1 or GLUT4, most preferably GLUT4.

By "translocation" of GLUT is meant the "migration" of GLUT from the interior of the cell to the cell membrane.

By "GRK" as used herein generally refers to a protein of the G protein-coupled receptor (serine/threonine) kinase (GRK) family. Presently, seven G protein-coupled receptor kinases have been discovered, which are named GRK1 to GRK7. In some embodiments, the GRK is GRK2.

As used herein, "a cell expressing a GRK" or "cells expressing a GRK", or "cells that express a GRK", etc. generally refer to cells that are also able to activate said GRK, unless the contrary is apparent from the context or indicated.

"A cell expressing GLUT" or "cells expressing GLUT", or "cells that express GLUT", etc. generally refer to cells that are also able to translocate GLUT, unless the contrary is apparent from the context or indicated.

A mammal is any mammal including humans, laboratory animals, domestic pets and farm animals. Preferably, the mammal is a human.

A "classical secondary messenger" as referred to herein e.g. may be selected from to diacylglycerol (DAG), phosphatidylinositols (PI), cyclic adenosine monophosphate (cAMP), cyclic guanosine monophosphate (cGMP), inositol trisphosphate (IP3), calcium ion ($Ca^{2+}$) and the gases nitric oxide (NO), carbon monoxide (CO) and hydrogen sulphide ($H_2S$). In some embodiments, the classical secondary messenger is selected from DAG, $Ca^{2+}$ and cAMP. In some particular embodiments, the classical secondary messenger is cAMP.

By "response of a classical secondary messenger", as used herein, is meant e.g. the presence of the classical secondary messenger in the cell, e.g. measured as the amount, content or concentration of the messenger, or any other parameter representative for the quantity of the messenger within a cell. The presence may be e.g. the presence in the cell, or the presence in the cytosol of the cell or within a compartment or organelle of the cell. Measurement of classical secondary messengers is well known in the art as exemplified in (Gusovsky 2001) and (currentprotocols.com/WileyCDA/). As an alternative, the response of a classical secondary messenger may be any downstream response, e.g. an activity of a cellular molecule stimulated by the presence of the classical secondary messenger.

A "response of a GRK" as used herein, generally may refer to a GRK activity. The activity of a GRK can be measured using any of a variety of assay kits, such as are commercially available from different suppliers, e.g. from Cell Signaling Technology, Inc. Since GRKs are kinases, an assay for measuring their activity basically is a kinase assay, as is well-known to the person of ordinary skill in the art. A response of a GRK also may refer to an increase of phosphorylation of the GRK itself.

By GPCR as referred to herein is meant any G protein coupled receptor. Adrenergic receptors are considered prototypical for GPCRs and have been investigated extensively (Santulli, Iaccarino 2013, Drake, Shenoy & Lefkowitz 2006). In some embodiments, therefore, the GPCR is an adrenergic receptor (AR). In some particular embodiments, the GPCR is an alpha-AR. In some embodiments, the GPCR is an $\alpha_1$-AR. In some other embodiments, the GPCR is an $\alpha_2$-AR. In still other embodiments, the GPCR is a $\beta$-AR. In some embodiments, the GPCR is a $\beta_1$-AR. In other embodiments, the GPCR is $\beta_2$-AR. In other embodiments, the GPCR is a $\beta_3$-AR In some embodiments, using assay systems measuring GRK response, e.g. GRK phosphorylation or activity, response of a classical secondary messenger, and GLUT response, e.g. GLUT4 response, the person of ordinary skill in the art can screen drug libraries such as commercial drug libraries and the like to select a compound with therapeutic concentration that activates GRK without causing a response from a classical secondary messenger and that increases glucose uptake in e.g. skeletal muscle model systems preferably without insulin present.

In some embodiments, in order to verify whether the contacting causes a response of a GRK in cells brought into contact with the compound, the method also comprises bringing the compound into contact with cells that express the GPCR but that do not express the GRK, and determining a difference in at least one effect caused by the contacting, between the cells expressing the GRK and the cells not expressing the GRK For example, in some embodiments, cells are transfected with siRNA directed against a GRK, e.g. GRK2. The screened compound is then brought into contact with transfected and untransfected cells, respectively and the uptake of a hexose such as glucose is measured in the cells. The absence of a significant difference in glucose uptake between cells expressing GRK2 and cells not expressing GRK2 not, indicates that the compound does not cause a GRK2 response.

In other embodiments, in order to verify whether the contacting causes a response of the GRK in cells brought into contact with the compound, the method also comprises bringing the compound into contact with cells that express the GPCR and the GRK, in the absence or presence of an inhibitor for the GRK, and verifying whether there is a significant difference in an effect of the GRK activity, such as uptake of a hexose in the presence or absence of GRK inhibitor.

The key concept of the present invention pertains to the ability of GPCRs to increase cellular effects, such as glucose uptake, through GRKs without stimulating classical secondary messengers (i.e. causing a response in a classical secondary messenger) in cells. The glucose uptake can be through GLUT of any of the fourteen members of the GLUT1-14 but is preferably GLUT1 or GLUT4, in particular GLUT4. The cells are any mammalian cells that express GLUT, but preferably cells expressing GLUT1 or GLUT4, in particular GLUT4.

A major problem with obesity and type 2 diabetes is that peripheral tissues become insulin resistant and glucose uptake is blunted. According to the present invention, this can be treated with compounds that stimulate GRKs and upregulate glucose uptake in peripheral tissues. Upregulating glucose uptake via compounds that stimulate GRKs without stimulating classical secondary messengers reduces requirement of insulin or insulin mimetic drugs. Accordingly, the incidence of life threatening complications of obesity and type 2 diabetes can be reduced. Such approach could also be therapeutically useful in other human diseases that are induced by, regulated by, or associated with, changes in glucose homeostasis.

As noted herein, conditions involving a dysregulation of metabolism, in particular, dysregulation of glucose homeostasis or glucose uptake in a mammal according to the present invention comprise any diseases induced by, regulated by, or associated with a dysregulation of glucose homeostasis or glucose uptake in a mammal. Such diseases may be e.g. Alzheimer's disease, blindness, cardiovascular disease, central nervous system diseases, diabetes, dyslipidemia, hypertension, kidney disease, macular degeneration, metabolic disorders, neurodegenerative diseases, obesity, peripheral neuropathy, reduced fertility, infertility, retinopathy, stroke, vascular disease, etc.

In some embodiments, such diseases are selected from metabolic syndrome, obesity, and diabetes, e.g. type 1 diabetes or type 2 diabetes. In some other embodiments, such diseases are selected from type 1 diabetes and type 2 diabetes, preferably type 2 diabetes.

Another aspect relates to methods for the treatment of a condition involving a dysregulation of glucose homeostasis or glucose uptake in a mammal. In particular, this aspect is directed to methods of preventing, curing or inducing durable long term remissions in mammals suffering from any such condition, or mammals that are susceptible to develop any such condition, as well as any other mammalian condition in which glucose homeostasis and glucose uptake into cells contribute to the condition. The invention is in particular concerned with the ability of GPCRs to increase glucose uptake through GRKs as a mechanism for treating a mammalian disease.

As noted herein above, a defective functioning of glucose uptake has been linked to various mammalian disorders.

Accordingly, one aspect relates to a method for treatment of a condition involving a defective functioning of glucose uptake in a tissue of a mammal, by improving the glucose uptake in said tissue.

Conditions involving a defective functioning of glucose uptake in a tissue of a mammal e.g. may be selected from such diseases Alzheimer's disease, blindness, cardiovascular disease, central nervous system diseases, diabetes, dyslipidemia, hypertension, kidney disease, macular degeneration, metabolic disorders, neurodegenerative diseases, obesity, peripheral neuropathy, reduced fertility, infertility, retinopathy, stroke, vascular disease etc.

Further, one aspect relates to methods of restoring or enhancing glucose uptake in tissues by translocation of GLUT, said translocation being achieved by stimulating GPCRs in such a way that said receptors stimulate GRK without causing a response in classical secondary messengers.

Depending on the cellular context, any of the mentioned activities will lead to alteration and/or increase in the GPCR signaling cascade coupled to glucose uptake, resulting in improvements relevant to the disease states of interest as will be discussed in detail herein below.

The method of the invention involves the stimulation (i.e. enhancement or increase) of a GLUT response in the form of GLUT translocation, preferably GLUT1 or GLUT4 translocation. Translocation of GLUT generally promotes uptake of a hexose such as glucose and alters cell and tissue functions particular to the specific target tissues including heart muscle, skeletal muscle and others tissues expressing various GLUTs. Methods that promote specific GLUT translocation by stimulating specific receptors in specific tissues can target or prevent specific diseases involving those specific tissues or cells. For example, stimulation of GLUT4 translocation in white adipocytes and skeletal muscle will improve glucose homeostasis. Drugs that stimulate GLUT4 translocation will thus improve, prevent, or cure different conditions involving a dysregulation of glucose homeostasis or glucose uptake in a mammal, in particular type 2 diabetes. Further, the functional activity of GLUT4 translocation can be modulated in human beings and other mammals in order to ameliorate or even prevent diabetes and reduce the need for other medicaments.

Thus, in one embodiment of the invention, there is provided a method of treatment of a mammal subject, preferably a human, suffering from or susceptible to develop a disease that is induced by, regulated by, or associated with, changes in glucose homeostasis, by a compound that upregulates translocation of GLUT, e.g. GLUT4, in peripheral tissues of said subject.

As noted herein above, GLUT4 is mainly expressed in heart, skeletal muscle and fat (white fat, brown fat and brite/beige), but GLUT4 has also been reported to be expressed in brain, kidney, liver and other tissues. Regulation of GLUT4 translocation in either of these tissues will affect the function of these. An enhanced translocation of GLUT4 will help keeping glucose levels in the blood under control and prevent diabetes and related disorders that are modulated by GLUT4 translocation and glucose uptake. In another aspect an increase of GLUT1 translocation in brown fat will lead to increased glucose uptake from the blood to prevent diabetes and related disorders.

In another aspect an increase of GLUT1 and/or GLUT3 translocation in brain will lead to increased glucose uptake from the blood into brain, which may be useful in the treatment of degenerative diseases of the central nervous system such as Alzheimer's disease. Therefore, in one embodiment of the invention, a method for the treatment of a degenerative disease of the central nervous system, such as Alzheimer's disease, is provided, by administration of a GPCR ligand capable of stimulating translocation of GLUT, e.g. of GLUT selected from GLUT1 and GLUT3.

Impaired GLUT translocation also plays a role in muscle wasting and stimulation of GLUT translocation may reduce muscle wasting.

GLUT translocation also plays a role in feeding behaviour. Mice lacking GLUT4 develop problems with lipid and glucose homeostasis leading to changes in feeding behaviour. Therefore, in some embodiments of the invention, a method of treating muscle wasting or a disordered feeding behaviour is provided, or a method of treating disrupted lipid or glucose homeostasis, by administration of a GPCR ligand capable of stimulating translocation of GLUT, e.g. of GLUT4.

Further, GLUT, e.g. GLUT8, has been reported as involved in both male and female infertility. Therefore, in some embodiments of the invention, a method of treating male or female infertility is provided, by administration of a beta-adrenergic ligand capable of stimulating translocation of GLUT, e.g. of GLUT8.

In one aspect, the present invention relates to a method for the screening of a candidate compound for use in any of the above-mentioned methods of treatment. Thus, one aspect relates to methods for screening compounds that increase GLUT translocation in cells, including skeletal muscle cells, heart cells, brown fat cells, white fat cells, beta cells, brain cells, liver cells, reproductive cells and cells involved in reproduction, mammary cells, and essentially any cells of the body where GPCRs, and GLUT are expressed.

According to one aspect, the invention provides a method for identifying GPCR ligands that do not activate classical secondary messengers but stimulate GLUT translocation to the plasma membrane and glucose uptake, and which therefore will provide for a treatment for any condition involving a dysregulation of glucose homeostasis or glucose uptake in a mammal.

In some embodiments, the present invention relates to method of screening for a candidate compound for the treatment of a condition involving dysregulation of metabolism in a mammal, said method comprising:

bringing a compound into contact with cells that express a GPCR and that further express a GRK, determining whether the contacting causes a response of the GRK in cells brought into contact with the compound, determining a response of a classical secondary messenger in cells brought into contact with the compound; and identifying the candidate compound based on the determined responses.

In some embodiments, the present invention relates to a method of screening for a candidate compound for the treatment of a condition involving dysregulation of metabolism in a mammal, said method comprising:

bringing a compound into contact with cells that express a GPCR and that further express a GRK and a GLUT, determining a response of a GLUT in cells brought into contact with the compound, determining a response of a classical secondary messenger in cells brought into contact with the compound; and identifying the candidate compound based on the determined responses.

The response of a GLUT in the cells may be determined, e.g. by measuring the presence of a GLUT in the cell membrane of the cells or by measuring the uptake of a hexose, such as glucose, into the cells.

Thus, in some embodiments, the present invention relates to a method of screening for a candidate compound for the treatment of a condition involving dysregulation of metabolism in a mammal, said method comprising:
bringing a compound into contact with cells that express a GPCR and that further express a GRK and a GLUT,
determining whether the contacting causes a response of the GRK in cells brought into contact with the compound,
determining a response of a GLUT in cells brought into contact with the compound,
determining a response of a classical secondary messenger in cells brought into contact with the compound; and
identifying the candidate compound based on the determined responses.

In some embodiments, the method of screening of the invention allows to identify a candidate compound for use to improve glucose uptake in cells of mammal.

Depending on the disorder that it is desired to treat, the GLUT is selected from any of GLUT1-14, preferably from any GLUT within class I.

For example, in one embodiment, the screening method of the invention is directed to identifying a compound useful in the treatment of diabetes, e.g. type 2 diabetes, and the GLUT preferably is GLUT1 or GLUT4, more preferably GLUT4.

In another embodiment, the screening method of the invention is directed to identifying a compound useful in the treatment of a neurodegenerative disorder, and the GLUT is selected from GLUT1, GLUT3 and GLUT4, in particular GLUT1

In another embodiment, the screening method of the invention is directed to identifying a compound useful in the treatment of male or female infertility, and the GLUT is preferably GLUT8.

In another embodiment, the screening method of the invention is used to determine whether known drugs already in use for treating other diseases also promote GLUT through GPCRs and GRKs. This would reveal new mechanisms of action for old drugs that might provide for a novel medical use of the drug in human or mammalian diseases caused by or associated with failure of glucose uptake and GLUT translocation, such as insulin resistance, obesity, diabetes and complications resulting from these disorders.

In some embodiments, the screening method may include a preliminary screening of substances to identify compounds that bind to GPCRs, i.e. compounds that are GPCR ligands. Such preliminary identification of ligands for GPCRs may be accomplished using e.g. in silico methods or methods using preparations of plasma membrane from tissue. In such a preliminary screening, a cell free assay system based on protein-protein interaction can also be used, such as one using electrochemiluminescence.

Thus, by use of cell-free methods, compounds that bind GPCRs can be identified in a preliminary screening step. Preferable molecules identified in such a method are small molecules with a molecular weight less than or equal to 1000 Daltons. These compounds are then screened in the cell-based screening method as described herein.

The screening method according to the present invention is not limited to any particular compounds, i.e. the compound may be any pharmaceutically acceptable substance, e.g. a known pharmaceutical substance.

In one embodiment, compounds that are previously known GPCR ligands can be screened in the method of the invention, e.g. in order to identify such GPCR ligands that cause an increase in GRK activity and glucose uptake without activating classical secondary messengers.

A preferable compound for screening in the method of the invention is one that may be administered orally in order to enhance glucose uptake in peripheral tissues.

In the screening method a of the present invention, a cell-based system may be used that comprises (1) a cell capable of expressing a GPCR and a GRK, and (2) a cell capable of expressing a GPCR, a GRK and a GLUT, preferably GLUT1 or GLUT4, in particular GLUT4, in reaction to a signal from the GPCR.

Such cells may be derived from primary cultures from heart, skeletal muscle, brown fat, white fat, brite/beige fat, liver, brain, mammal gland and other mammalian tissues. The cell or cells to be used in the screening method generally is selected so as to be representative of the tissue(s) involved or afflicted by the condition, disease or disorder. For example, if the screening method is directed to identifying a compound useful in the treatment of a neurodegenerative disorder, the cell suitably is selected from mammalian nerve cells or cells representative of mammalian nerve cells or cells that may have an importance in the functioning of the mammalian nervous system, in particular in the transportation of glucose into the mammalian nervous system, e.g. into the brain. Likewise, if the screening method is directed to identifying a compound useful in the treatment of a metabolic disorder, such as diabetes, the cell suitably is selected from mammalian muscle cells or cells representative of mammalian muscle cells, in particular mammalian skeletal muscle cells.

Examples of cell lines that can be utilized include heart cell lines such as H9c2, VH 2, skeletal muscle cell lines, such as L6, L8, C2C12, fat cell lines, such as HIB cells, 3T3-L1, 3T3 F442 and other cell lines, well known to the person of ordinary skill in the art.

Cell lines of different origin with GPCRs and GRKs and/or GLUT can also be utilized. Although a number of cell types can be used for this process, one that can be transfected and express (or overexpress) GPCRs and GRKs and/or GLUT would be preferable, for example CHO cells. The introduced GPCR and/or GLUT could be stably transfected or non-stably transfected according to methods well known to investigators of skill in the art.

In some embodiments of a screening method according to the invention, the cell is grown in a cell culture medium, transferred into a sample well of a conventional microplate having e.g. 8, 12, 24, 48, 96, 384 or 1536 sample wells, cell differentiation is induced by addition of a differentiation medium, and the cell is allowed to differentiate for a suitable time period. The cell is then brought into contact with the compound to be screened for a predetermined time period, of e.g. 5 minutes to 10 hours, or 0.5 hour to 5 hours, e.g. 1 hour to 3 hours.

The compound to be screened in the assay generally is provided dissolved in a liquid phase, which e.g. may be an aqueous phase, such as purified water or a suitably buffered and isotonic aqueous phase, or an organic solvent phase, or a mixture thereof. The compound is brought into contact with the cell at a concentration that suitably should correspond to an amount relevant for pharmaceutical use, e.g. a concentration of about $10^{-8}$ to $10^{-1}$ M, or $10^{-7}$ to $10^{-2}$ M, e.g. $10^{-6}$ to $10^{-3}$ M.

The candidate compound is identified based on a GRK response and classical secondary messenger response determined in cells brought into contact with the compound to be screened. Preferably, the screening method involves comparing the GRK response and the classical secondary messenger response, determined in cells brought into contact with the compound, with reference values.

Thus, in some embodiments, the GRK response determined in a cell brought into contact with a compound ($A_{comp}$) is compared to a suitable reference, e.g. the GRK response (Aref), determined for a similar cell which has not been brought into contact with the compound, such as a cell treated with buffer or vehicle only under similar conditions. In such case, for the compound to be contemplated as a candidate compound, invention, Acomp should generally be higher than Aref.

The reference value also may be the GRK response obtained when bringing cells expressing GRK into contact with a compound having a previously determined or known capacity of eliciting a GRK response, such as BRL 37344 or isoproterenol (it should be noted that isoproterenol, i.e. (RS)-4-[1-hydroxy-2-(isopropylamino)ethyl]benzene-1,2-diol, also is referred to as isoprenaline, and the two names are used interchangeably herein). Thus, in some embodiments, the GRK response determined for cells brought into contact with a compound to be screened (Acomp) is compared to the GRK response ($A_{agonist}$), determined for similar cells brought into contact with a compound known to activate a GRK, such as isoproterenol or BRL 37344.

In the screening method of the invention, the response P of a classical secondary messenger is determined by measuring or otherwise determining any variable representative for such response. For example, the amount of the classical secondary messenger of the cell, either the total amount, or the amount in some compartment of organelle, of the cell, may be measured, or the activity of any target molecule downstream of the classical secondary messenger may be determined.

In some embodiments, the maximum response Pcomp, of a classical secondary messenger, determined in cells brought into contact with a compound to be screened, is compared to a suitable reference, such as the response Pref (e.g. the concentration or amount) of the classical secondary messenger determined in similar cells that have not been brought into contact with the compound, such as cells treated with buffer only under similar conditions, or the classical secondary messenger response in cells that have been treated with a compound that is known not to elicit such a response, such a compound that elicits a GRK response, e.g. BRL 37344.

In some embodiments, Pcomp may be compared to the maximum response Pagonist, of a classical secondary messenger, determined for similar cells brought into contact with a compound known to elicit a response of a classical secondary messenger, such as isoproterenol.

Based on the above determinations, the screening method may permit to identify, as a candidate compound, a compound that causes an increase in activity of GRK in a cell, without causing a significant response of a classical secondary messenger in the cell. It should be realized some classical secondary messenger response in the cell in some cases may be tolerated.

In some embodiments, in order to identify a candidate compound, a difference $\Delta_1$ between Pcomp and Pref is calculated and should be as close to 0 as possible. For example, in order for a compound to be contemplated as a possible candidate compound, a ratio r $$r = \frac{Pcomp - Pref}{Pref}$$

may be calculated and a limit may be selected below which the compound is considered as a possible candidate compound. For example, a compound having a ratio r lower than 0.7, or lower than 0.5, or lower than 0.4, or lower than 0.3, or lower than 0.2, e.g. lower than 0.15, or lower than 0.1, may be contemplated as a candidate compound.

In some embodiments, the method also comprises determining a value Pagonist, e.g. by bringing cells in contact with isoproterenol and determining the contents of a classical secondary messenger in the cells. A difference $\Delta_2$ between $P_{agonist}$ and $P_{ref}$ may then be calculated, as well as a ratio r'

$$r' = \frac{Pagonist - Pref}{Pagonist}$$

The ratio r' should be as close to 1 as possible. For example, a compound having a ratio r' higher than 0.1, or higher than 0.2, or higher than 0.3, or higher than 0.4, or higher than 0.5, or higher than 0.6, or higher than 0.7, e.g. higher than 0.8, or higher than 0.9, may be contemplated as a candidate compound.

As an alternative, cells may be brought into contact with the compound to be screened and a compound known to increase the presence of a classical secondary messenger (e.g. isoproterenol), respectively, and Pcomp and Pagonist may be determined. A ratio r"

$$r'' = \frac{Pcomp - Pref}{Pagonist - Pref}$$

may then be calculated. Thus, in some embodiments, a compound having a ratio r" lower than 0.7, or lower than 0.5, or lower than 0.4, or lower than 0.3, or lower than 0.2, e.g. lower than 0.1, may be contemplated as a candidate compound.

In some embodiments, in order to calculate r, r' or r", any A (Acomp, Aref) or P (Pcomp, Pref, Pagonist) is indicated as a percentage of a basal value, i.e. the value determined for cells that have not been brought into contact with any compound, e.g. untreated cells or cells brought into contact with vehicle only.

In order to identify a compound as a candidate compound, the classical secondary messenger response Pcomp determined in cells brought into contact with a compound at any given concentration preferably should be considered in relation to the GRK response Acomp determined in cells brought into contact with the compound at the same concentration and under similar conditions.

Any pair of Pcomp and Acomp values may also be compared to values obtained under similar conditions using a compound known to elicit GRK response without eliciting a response of a secondary classical messenger, such as the compound BRL 37344, and/or a compound known to elicit GRK response while also eliciting a response of a secondary classical messenger, such as isoproterenol. A ratio $$r_{comp} = \frac{Acomp}{Pcomp}$$

or any similar ratio putting the obtained GRK response in proportion to the elicited classical secondary response, may be calculated for the screened compound, and compared to a similar ratio $r_{ref}$ calculated for a reference compound. If $r_{comp}$ is equal to or higher than $r_{ref}$, e.g. when the reference compound is BRL 37344, this may be taken as an indication that the compound is a candidate compound.

It should be realized that the identification of the candidate compound based on the determined GRK activity and presence of classical secondary messenger is not limited to any of the above calculation methods, which are provided as examples only.

For example, the candidate compound may be identified without calculating any particular ratio, e.g. by simple visual inspection of results of e.g. western blots.

In some embodiments, the inventive method comprises measuring protein phosphorylation of a target downstream classical secondary messenger in order to verify that bringing the compound into contact with the cell does not lead to a classical secondary messenger response with consequent activation of downstream pathway. For example, phosphorylation of protein kinase A (PKA) may be measured using a suitable kinase assay.

In some embodiments, the screening method of the invention also comprises determining a GLUT response in cells brought into contact with the compound.

For example, as GLUT response, the GLUT translocation may be measured by use of a method as described in (Koshy et al. 2010). GLUT translocation also may be measured by the method exemplified herein below.

It is well known that GLUT translocation, in particular GLUT4 translocation, leads to glucose uptake in certain tissues, mainly skeletal muscle and fat. In one embodiment, therefore, uptake of a hexose, such as glucose, from the cell medium is used as an indicator of GLUT translocation, e.g. GLUT4 translocation.

Based on the results a candidate compound may be identified as one causing a GLUT response, e.g. an increase of the GLUT translocation, compared to the reference value for the GLUT translocation, e.g. the GLUT translocation measured under similar conditions for a cell that has not been brought into contact with the candidate compound, e.g. a cell that has been brought into contact only with the liquid solvent phase or vehicle for the candidate compound.

The same type of calculations as for the GRK activity may be made, e.g. the glucose uptake of cells brought into contact with the compound may be compared with the glucose uptake of cells brought into contact with e.g. insulin, isoproterenol, BRL 37344 or any other suitable reference compound.

The screening method may be performed using one target cell type, representative for one or more particular tissues of a mammalian body. The screening method however may be expanded to any number of different cells, thereby allowing for the verification of a selectivity of the compound for a target cell type and/or the absence of stimulation classical secondary messenger in the target cell type as well as in other mammalian cell types.

Thus, in some embodiments, the screening method of the invention is performed using more than one cell type representative for a tissue of a mammalian body. For example, a screening method of the invention may involve the use of a panel of cells selected from mammalian cells, e.g. selected from muscle cells, adipocytes, such as brown fat cells and white fat cells, beta cells, brain cells, liver cells, reproductive cells and cells involved in reproduction, and mammary cells.

In some embodiments, the effect of brining the compound into contact with the cells may thus be compared between different cell types, e.g. to identify a compound that preferentially stimulates GRK activity and GLUT translocation in some cell types over others.

In some embodiments, when the screening method is performed on a panel of different cells, at least one cell is a muscle cell, and at least one other cell is not a muscle cell.

For example, in one embodiment, the screening method is a method for identifying a candidate compound for use in the treatment of a condition involving a dysregulation of glucose homeostasis or glucose uptake in a tissue having cells that contain GLUT4 as a glucose transporter, in particular muscles, such as in particular skeletal muscles, but also cardiac muscle.

In another embodiment, the screening method is a method for identifying a candidate compound for use in the treatment of a condition involving a dysregulation of glucose homeostasis or glucose uptake in a tissue having cells that contain GLUT1 as a glucose transporter, such as the epithelial cells of the blood-brain barrier.

A drug that stimulates a GPCR and does not increase classical secondary messenger activity but GLUT translocation might work on all tissues of the body, or display tissue specificity. The effect (s) of either known or unknown drugs on translocation of any GLUT, e.g. GLUT4 can be further assessed in vivo, e.g. by constructing a mouse that expresses GPCR and/or GLUT containing a tag preferable a fluorescent protein. After administration of the compounds to the test animal, all tissues can be evaluated for GPCR activation and GLUT translocation.

By the screening method of the present invention, compounds may be identified that are useful for the treatment of any condition involving a dysregulation of glucose homeostasis or glucose uptake in a mammal. In one aspect, thus a compound is provided, suitable for use in the treatment of a condition involving a dysregulation of glucose homeostasis or glucose uptake in a mammal, which is a compound that does not cause an increase of the classical secondary messenger production in the cells of the mammal, but that causes an increase of the GLUT translocation in at least some cells of the mammal, in particular in muscle cells, such as skeletal muscle cells.

One aspect of the invention is a kit for use in a method of screening for a candidate compound for the treatment of a condition involving a dysregulation of metabolism in a mammal, said kit comprising cells capable of expressing a GPCR, which cells are further capable of expressing a GRK, together with instructions for use of the kit.

In one embodiment, the kit comprises a cell capable of expressing a GPCR, and of producing glucose uptake in reaction to a signal from the GPCR, and (2) a cell capable of expressing a GPCR and of translocating a GLUT, preferably GLUT1, GLUT3 or GLUT4, in particular GLUT1 or GLUT4, most preferably GLUT4, in reaction to a signal from the GPCR.

Such cells may be derived from primary cultures from heart, skeletal muscle, brown fat, white fat, brite/beige fat, liver, brain, mammal gland and other mammalian tissues. The cell or cells to be used in the kit generally is selected so as to be representative of the tissue(s) involved or afflicted by the condition, disease or disorder. For example, if the kit is for use in a screening method directed to identifying a compound useful in the treatment of a neurodegenerative disorder, the cell suitably is selected from mammalian nerve cells or cells representative of mammalian nerve cells or cells that may have an importance in the functioning of the mammalian nervous system, in particular in the transportation of glucose into the mammalian nervous system, e.g. into the brain. Likewise, if the kit is for use in a screening method directed to identifying a compound useful in the treatment of a metabolic disorder, such as diabetes, the cell suitably is selected from mammalian muscle cells or cells representative of mammalian muscle cells, in particular mammalian skeletal muscle cells.

Examples of cell lines that can be used in the kit of the present invention include heart cell lines such as H9c2, VH 2, skeletal muscle cell lines, such as L6, L8, C2C12, fat cell lines, such as HIB cells, 3T3-L1, 3T3 F442 and other cell lines, well known to the person of ordinary skill in the art.

Cell lines of different origin with introduced GPCR, GRK and/or GLUT can also be included in the kit of the invention, e.g. a cell that is transfected and expresses (or overexpresses) GPCR, GRK and/or GLUT, for example a CHO cell line.

In some embodiments, the kit also comprises cells expressing a GPCR and preferably a GLUT, which cells are transfected with siRNA directed against a GRK.

In another aspect, a compound is provided, suitable for use in the treatment of a condition involving a dysregulation of glucose homeostasis or glucose uptake in a mammal which is a compound that does not cause a classical secondary messenger response (e.g. an increase content of classical secondary messenger) in the cells of the mammal, that causes an increase of the GLUT translocation in at least some cells of the mammal, in particular in muscle cells, such as skeletal muscle cells, and that does not cause an increase of the GLUT translocation in other cells of the mammal, in particular adipocytes, such as white fat cells.

One aspect of the present invention relates to a method of treatment of a condition involving a dysregulation of glucose homeostasis or glucose uptake in a mammal, comprising the administration of a therapeutic effective amount of one or more compounds that bind GPCR, said binding causing an increase of GRK activity and GLUT translocation in cells of the mammal, in particular muscle cells of the mammal, without causing any significant classical secondary messenger response in the cells of the mammal, to a mammal in need of such treatment.

Another aspect of the present invention relates to the use of a compound identified in a screening method of the present invention, in the manufacturing of a medicament for use in the treatment of a condition involving a dysregulation of metabolism, e.g. dysregulation of glucose homeostasis or glucose uptake in a mammal.

Still another aspect relates to a pharmaceutical composition comprising a compound identified in a screening method of the present invention. Still another aspect relates to a compound identified in a screening method of the present invention.

Therapeutically effective means an amount of compound which is effective in producing GLUT translocation. Administration means delivering the compound of the present invention to a mammal by any method, for example, orally, intravenously, intramuscularly, topically, transdermal, or inhalation.

Carriers for the administration include any carrier known in the art including water, saline, phosphate buffered saline, dextrose, glycerol, ethanol and similar carriers and combination of these. Carriers can also comprise wetting or emulsifiers, preservatives or buffers that enhance effectiveness, half-life, and shelf life of the compound(s).

Furthermore additional carriers influencing the release of the compound(s) including how quick, sustained or delayed the active compound(s) is released when administered to the mammal.

The composition of this invention can be any form including solid, semi-solid and liquid such as used in tablets, pills, powders, solutions, dispersions, suspensions, liposomes suppositories, injections and infusible solutions.

The methods and compositions of the invention can be administered to any suitable mammal such as rabbit, rat or mouse or more preferable a human.

The invention is further illustrated by the following non-limiting examples.

EXAMPLES

Example 1

Soleus muscles were dissected from Sprague-Dawley rats and suspended in Krebs-Henseleit bicarbonate (KHB) buffer (118.5 mM NaCl, 4.7 mM KCl, 1.2 mM $KH_2PO_4$, 25 mM $NaHCO_3$, 2.5 mM $CaCl_2$, 1.2 mM $MgSO_4$, 5 mM HEPES) in organ baths containing 30 ml KHB containing 5 mM glucose and 15 mM mannitol, bubbled with 95% $O_2$/5% $CO_2$ (pH 7.4) and maintained at 37° C. Incubation with KU0063794 or vehicle was for 30 min followed by insulin or isoproterenol for 1 h. Muscles were rinsed with KHB (20 mM mannitol) for 10 min, then incubated in KHB (8 mM 3-O-methylglucose and 12 mM mannitol with 438 µCi/mmol 3-O-methyl[3H]glucose (80.2 Ci/mmol; PerkinElmer) and 42 µCi/mmol [$^{14}$C] mannitol (58.8 mCi/mmol; PerkinElmer, USA)) for 12 min. Muscles were then rinsed with PBS and frozen in liquid nitrogen, weighed and dissolved in 1 mL of 0.5M NaOH at 60° C. $^3$H and $^{14}$C were measured by liquid scintillation counting. Total muscle 3-O-methylglucose and extracellular space were measured as described previously (Zierath 1995). Intracellular 3-O-methylglucose accumulation was calculated by: (Total muscle 3-O-methylglucose)−(extracellular 3-O-methylglucose)=intracellular 3-O-methylglucose. This was then expressed as a rate of 3-O-methylglucose transport per mL of intracellular water per hour. Glucose uptake was measured in L6 skeletal muscle cells and in human skeletal muscle cells (SKMC) grown in 12-well plates using $^3$H-2-deoxyglucose as previously described (Nevzorova et al. 2002) with minor modifications. L6 cells were differentiated for 7-8 days before the experiment, serum-starved over night in media containing 0.5% fatty-acid free BSA and stimulated with drugs for totally 2 h, unless otherwise stated. Inhibitors were added 30 min before stimulation. 25 min before the end of the experiment, cells were washed twice in warm PBS and kept in glucose-free DMEM together with the different drugs for 10 min before 50 nM $^3$H-2-deoxyglucose was added for additional 6 minutes. The reaction was terminated by washing the cells in ice-cold PBS three times. Cells were lysed in 0.2 M NaOH for 1 h in 60° C. and the radioactivity detected by liquid scintillation (scintillation buffer Emulsifier Safe, Perking Elmer and analysis is a Tri-Carb® 2800TR from Perkin Elmer).

Figure 1B:
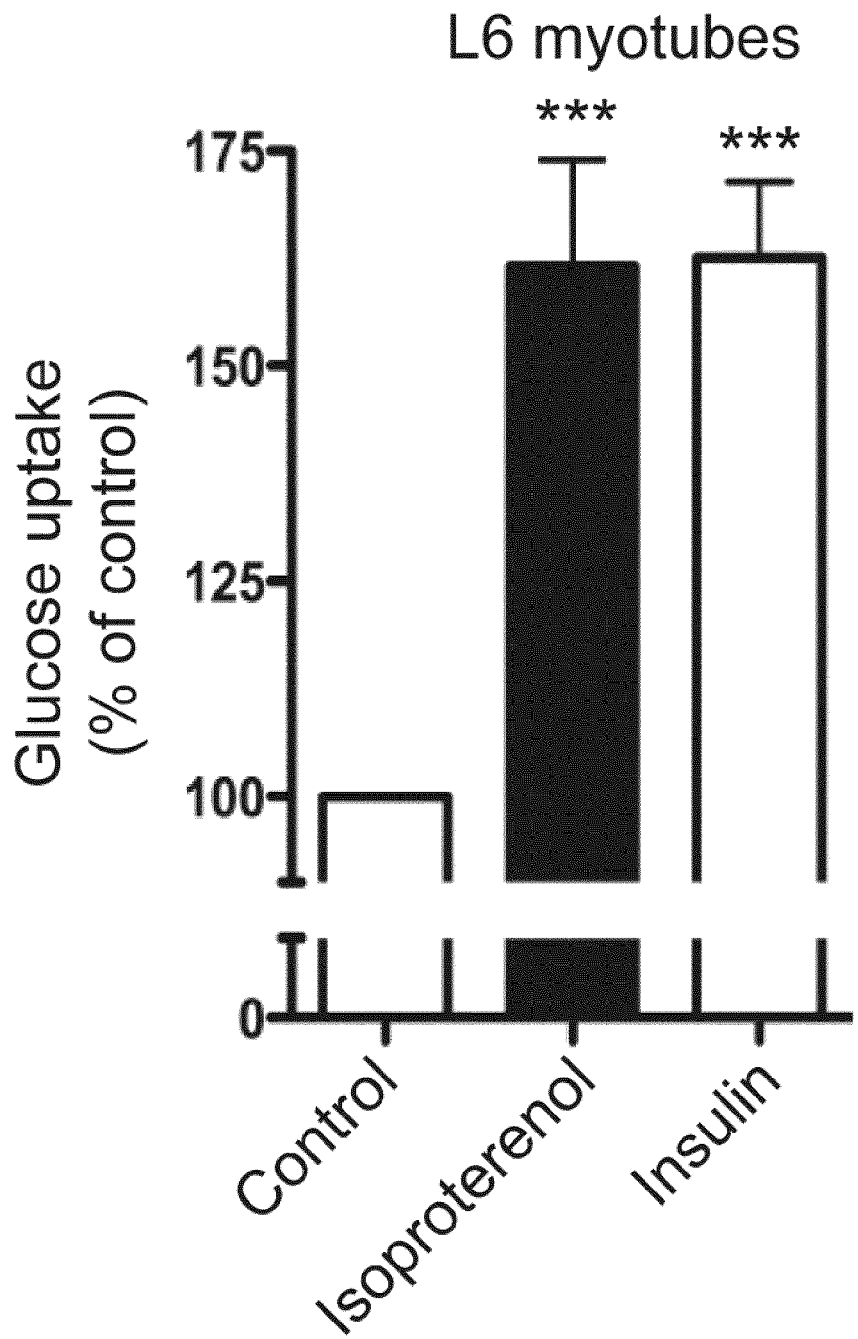
Figure 1C:
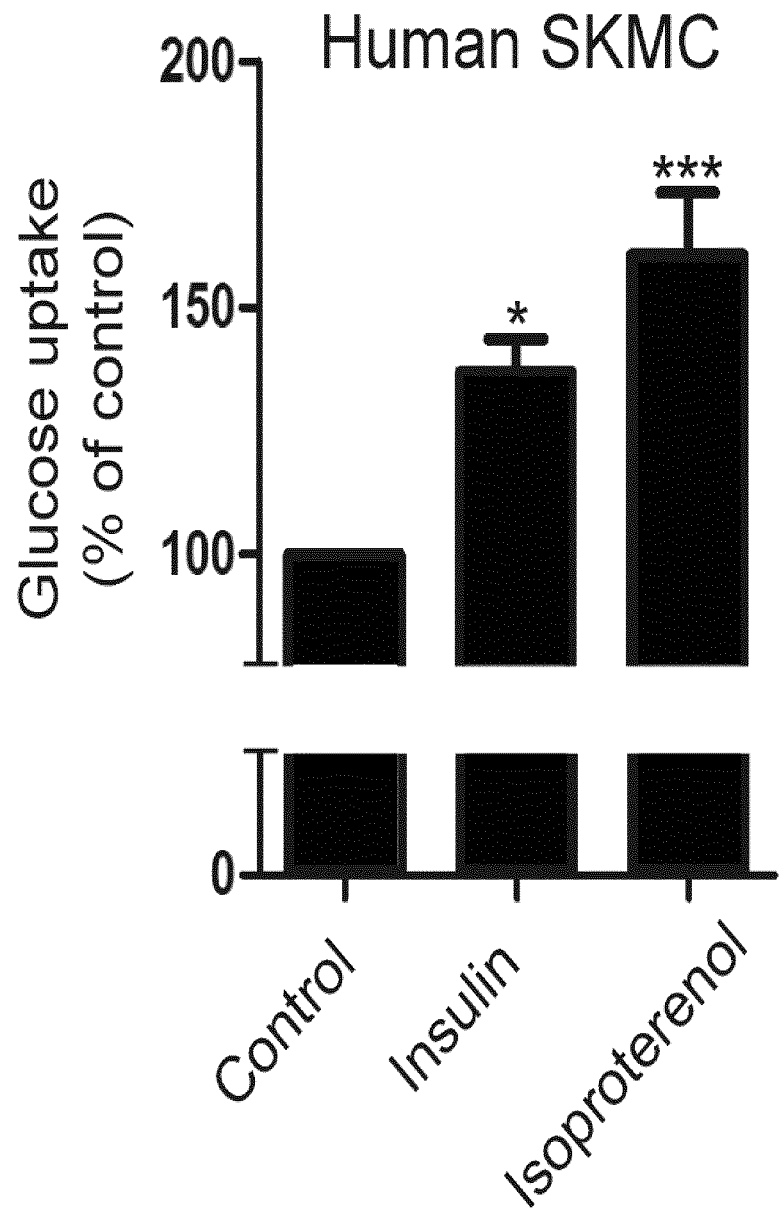

Stimulation with isoprenaline that stimulates the prototypical GPCRs in the beta-adrenergic family leads to glucose uptake in the peripheral skeletal muscle tissue and cells both in rats and humans (FIGS. 1A-1C).

Example 2

Figure 2A:
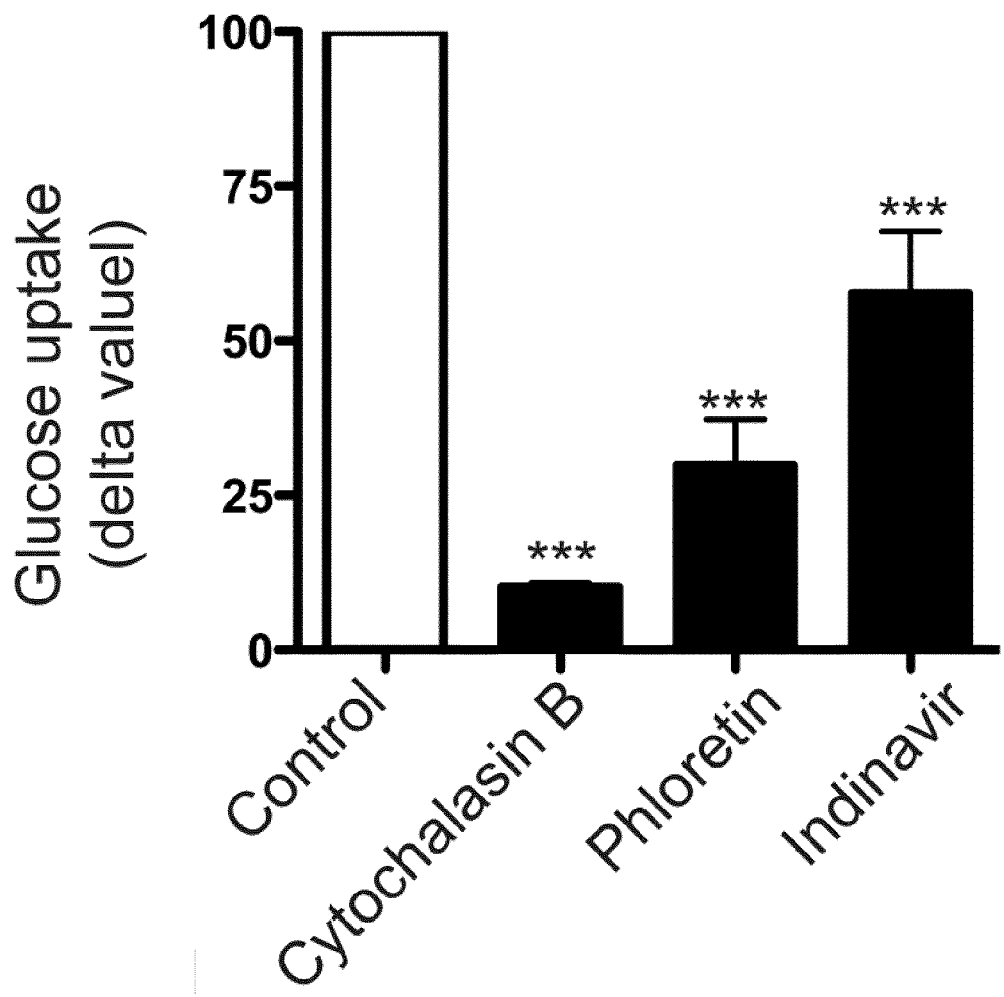
FIGS. 2A-2C are (2A) a bar chart showing glucose uptake (delta value) in L6 myotubes brought into contact with the general GLUT inhibitor cytochalasin B, the GLUT1/4 inhibitor phloretin, the GLUT4 inhibitor indinavir or, as a control, vehicle only; (2B) a bar chart showing glucose uptake (delta value) in L6 myotubes brought into contact with isoproterenol or insulin, in the absence or presence of phloretin; and (2C) a bar chart showing glucose uptake (delta value) in L6 myotubes brought into contact with isoproterenol or insulin, in the absence or presence of indinavir.
Figure 2B:
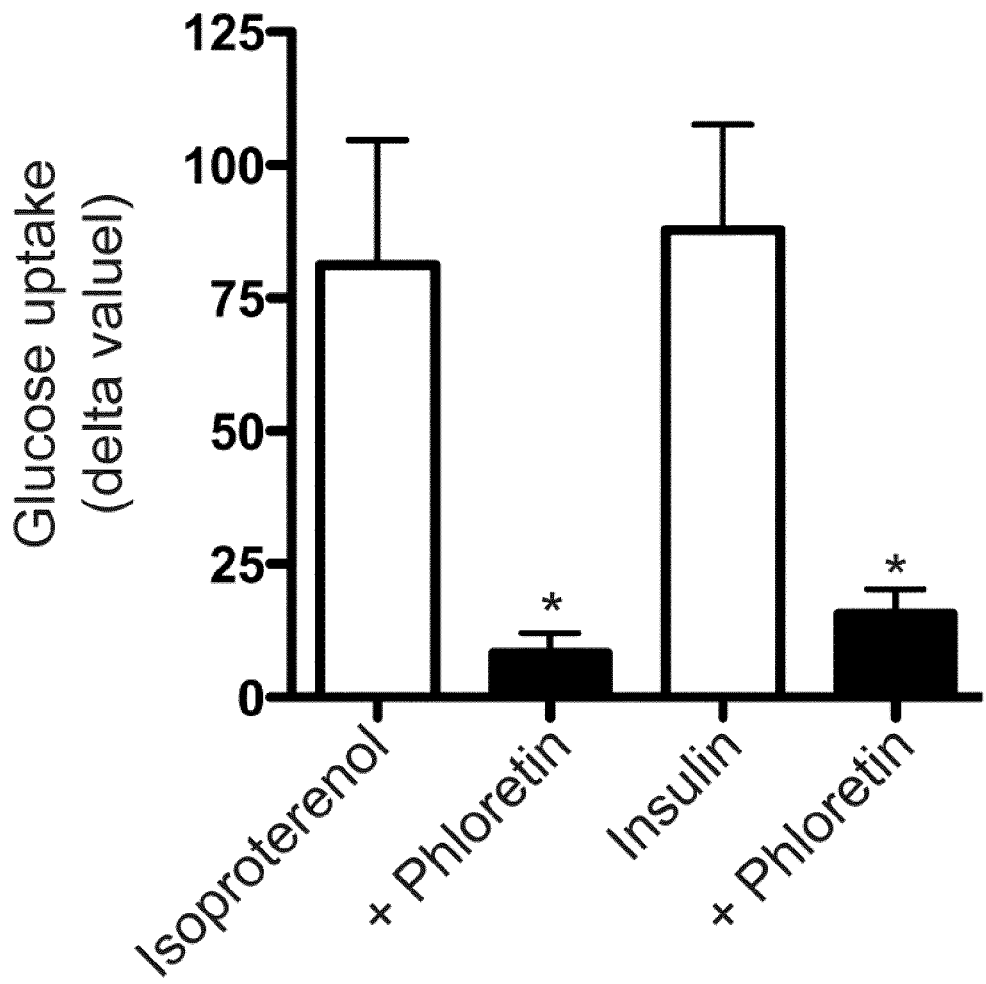
Figure 2C:
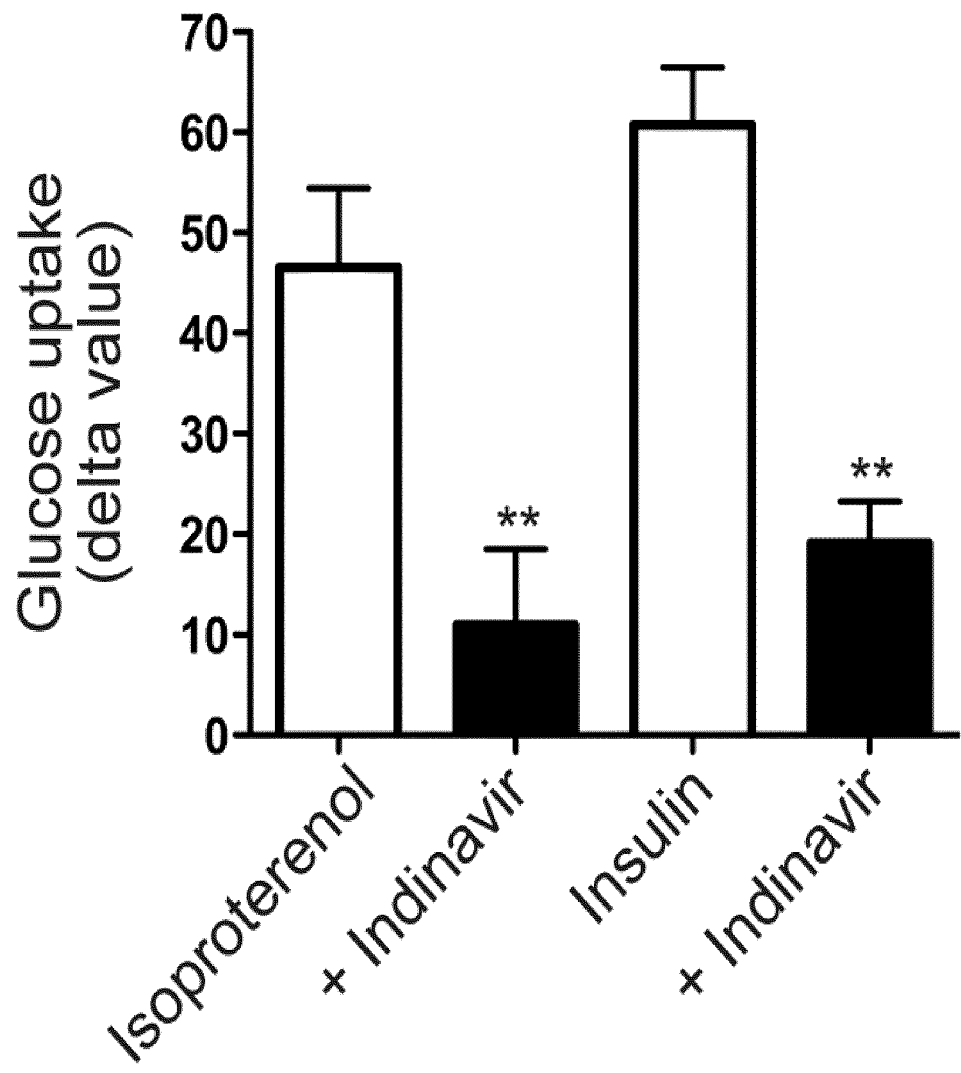

Cells were grown as in Example 1. Cells were pretreated with inhibitors for 30 min and then exposed to GPCR stimulation. To examine whether GLUTs were involved in GPCR stimulated glucose uptake (Taverna, Langdon 1973), experiments were performed with cytochalasin B. This compound reduced basal glucose uptake and glucose uptake in response to both insulin and GPCR stimulation (FIGS. 2A-2C), indicating that glucose uptake is dependent on GLUTs. To specify the GLUT isoform involved, the selective GLUT1/4 inhibitor phloretin and the GLUT4 inhibitor indinavir were used. Phloretin and indinavir blocked basal glucose uptake consistent with other studies in L6 myotubes (Murata, Hruz & Mueckler 2002) and significantly reduced both GPCR and insulin-stimulated glucose uptake suggesting a role for GLUTs, and specifically GLUT4.

Figure 3A:
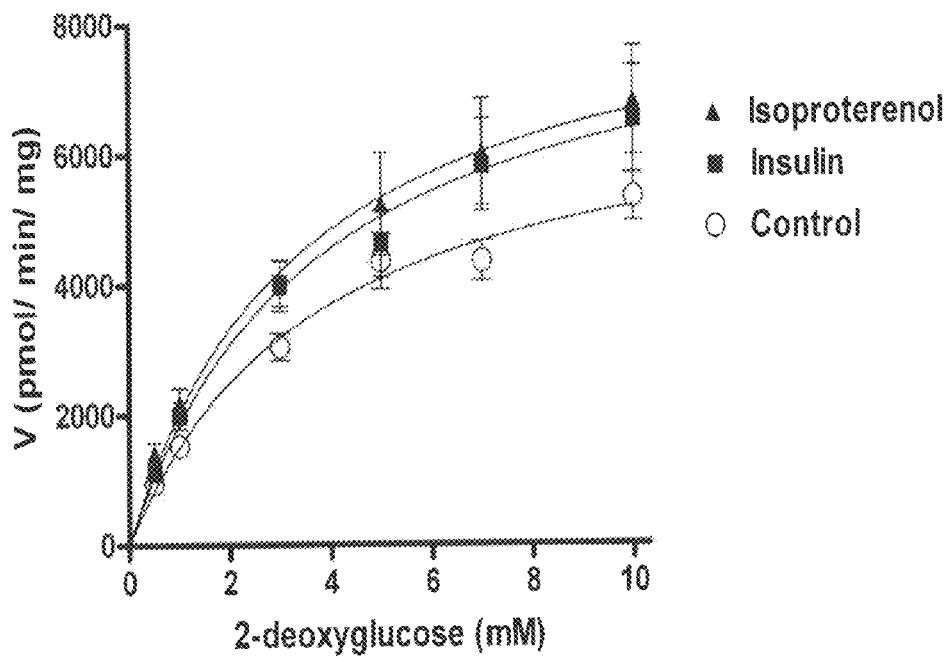
FIGS. 3A and 3B are (3A) a graph showing the rate v (pmol/min/mg) of uptake of 2-deoxyglucose by L6 myotubes in cell medium containing different concentrations of 2-deoxyglucose (mM), which myotubes are brought into contact with isoproterenol, insulin or, as a control, vehicle only; and (3B) a graph showing the corresponding Eadie-Hofstee plots of rate v against rate v divided by 2-deoxyglucose concentration [S].
Figure 3B:
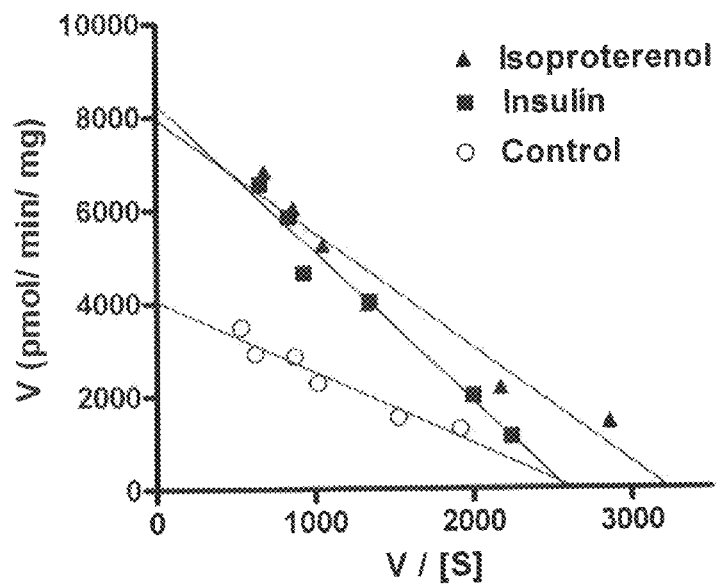
Figure 5A:
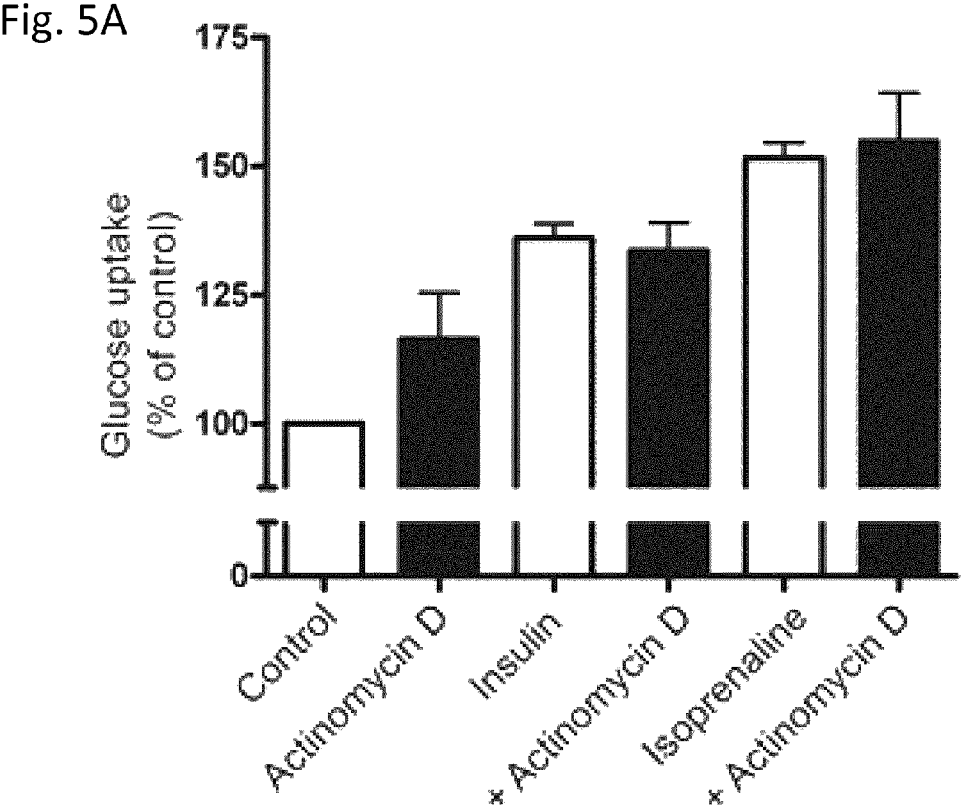
FIGS. 5A-5E are (5A) a bar chart showing glucose uptake (% of control) in L6 myotubes brought into contact with insulin, isoprenaline or, as a control, vehicle only, with or without treatment with the transcription inhibitor Actinomycin D; (5B) a bar chart showing the amount of GLUT4 mRNA (% of control) in L6 myotubes brought into contact with insulin, isoproterenol or, as a control, vehicle only, (5C) a bar chart showing glucose uptake (% of control) in L6 myotubes brought into contact with insulin, isoproterenol or, as a control, vehicle only, with or without treatment with the translation inhibitor cyclohexamide; (5D) a bar chart showing expression of GLUT4 protein (% of control) in L6 myotubes brought into contact with insulin, isoprenaline or, as a control, vehicle only, and (5E) a western blot of GLUT4 from L6 myotubes brought into contact with insulin, isoprenaline or, as a control, vehicle only.
Figure 5B:
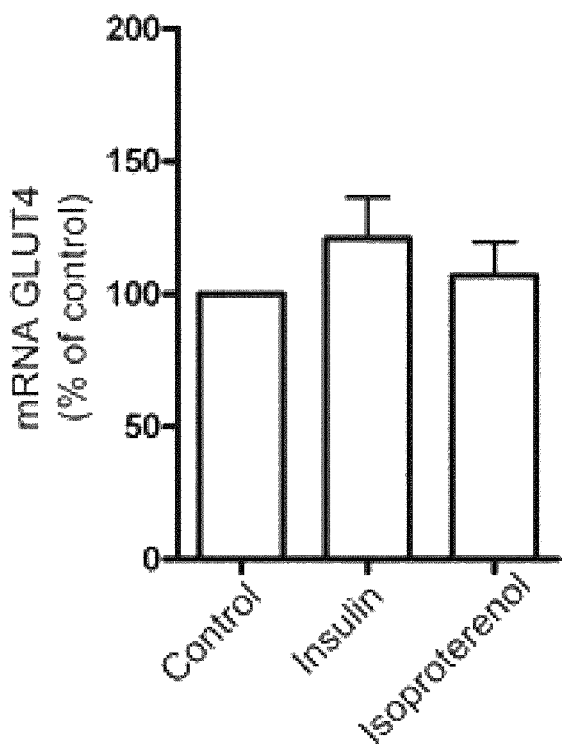
Figure 5C:
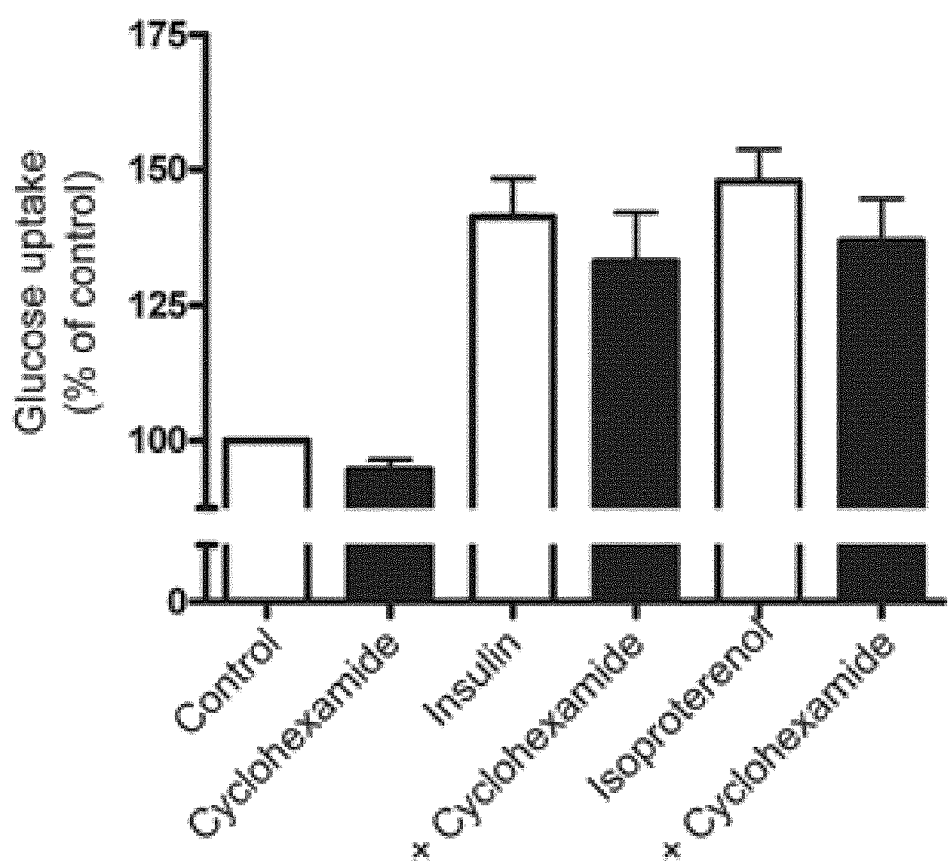
Figure 5D:
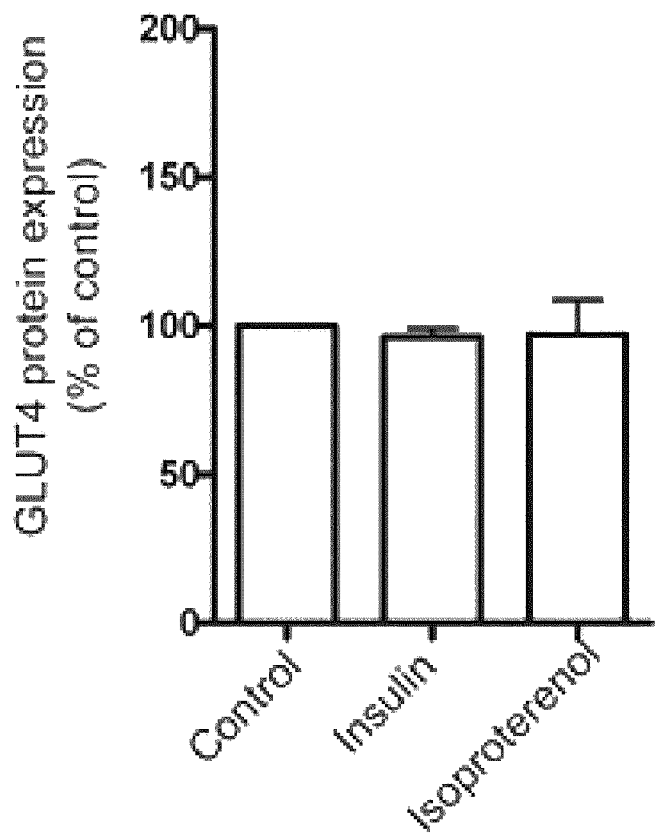
Figure 5E:
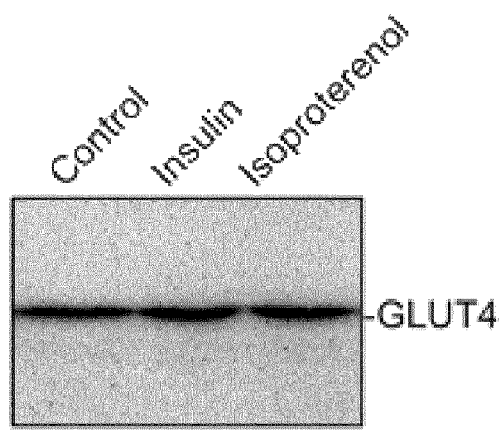

To examine whether GPCR stimulated glucose uptake was carrier-mediated, kinetic studies were performed with increasing concentrations of 2-DOG (Sobel, Wolfson & Krulwich 1973). Insulin increased glucose uptake with Km values as previously reported (FIGS. 3A and 3B) (Sarabia, Ramlal & Klip 1990). GPCR stimulated glucose uptake also followed a classical Michaelis-Menten curve with Km values similar to that of insulin, indicating that this also involves transporter proteins (Ploug et al. 1987) (FIGS. 3A and 3B). That GPCR stimulated glucose uptake was through GLUTs was confirmed using siRNA directed against GLUT4 that significantly reduced both insulin and GPCR mediated glucose uptake compared to a scrambled siRNA (FIGS. 4A and 4B). L6 myotubes (differentiated for 7 days) or L6 myoblasts or human SKMC cells in 12-well plates were transfected by electroporation, washed with PBS and detached from the wells by 5 minutes incubation with 0.25% trypsin/EDTA at 37° C. The cells then were transferred to Eppendorf tubes and pelleted by centrifugation at 1000×g for 3 minutes. Cells were resuspended in 20 µl/well of SE Cell Line Nucleofector solution for the L6 cells and P1 primary Nucleofector solution for the SKMC, with the supplied supplement (Lonza) and 100 pmol of siRNA (L6 myotubes) or 0.8 µg GLUT4mycGFP construct (L6 myoblasts and human SKMC) were added. siRNA constructs used were consisted of a sequence directed against rat GLUT4 or siRNA containing a control sequence. For each electroporation, cells were placed in 16-well microcuvette plate (Lonza). After electroporation with the Amaxa™ 4D-Nucleofactor™ system (Lonza) 80 µl of pre-warmed RPMI1640 media were added to the each microcuvette well, then transferred to the Eppendorf tubes containing DMEM supplemented with 10% FBS. 8 hours after transfection, medium was changed to serum free media (DMEM supplemented with 0.1% BSA, 4 mM L-glutamine, and 100 Units/ml penicillin, 100 µg/ml streptomycin, and 10 mM HEPES) and incubated overnight. 24 hours after transfection, glucose uptake, immunocytochemistry or western blot was performed as described above.

In conclusion GLUT4 is involved not only in insulin mediated glucose uptake, but also in GPCR mediated glucose uptake.

Example 3

There are a number of mechanisms that can increase glucose uptake, including transcription and translation of glucose transporters. In order to test if transcription and translation are involved in GPCR stimulated glucose uptake L6 skeletal muscle cells were grown in 6-well plates and differentiated for 7 days. Cells were harvested in 1 mL Ultraspec™ RNA isolation reagent (Biotecx Laboratories Inc. Houston, Tex., USA) and RNA isolated according to the manufacturer's instructions. Total RNA was dissolved in DEPC-water (Invitrogen) and quantified in a DU-50 Beckman (Fullerson, Calif.) spectrophotometer. Total RNA was reverse transcribed by the High Capacity cDNA Reverse transcriptase kit (Applied Biosystems, Inc., Carlsbad, Calif., USA). Random hexameres were used for first-strand cDNA synthesis. Primers for GLUT1, GLUT4 and TFIIB as endogenous control were designed by Universal Probe Library (Roche Applied Science) for primer and purchased from Invitrogen. SYBR®GREEN PCR Master Mix (Applied Biosystems, Inc., Carlsbad, Calif., USA) was mixed with reference dye and primers and loaded on a MicroAmp® Optical 96-Well Reaction Plate with Barcode (Applied Biosystems). 2 µl of template cDNA were added in duplicates. TFIIB were used as an endogenous control.

During certain circumstances, glucose uptake can be elevated by de novo synthesis of GLUTs through increases in transcription and/or translation rates. Treatment with the general transcription inhibitor actinomycin did not significantly affect basal glucose uptake or cell viability, or insulin- or GPCR-mediated glucose uptake at 2 h (FIGS. 5A-5E), indicating that transcription is not involved in GPCR stimulated glucose uptake at the time points investigated. In agreement with this, GLUT4 mRNA levels were not elevated by GPCR treatment. The general translational inhibitor cyclohexamide did not affect basal glucose uptake or cell viability, or either insulin- or GPCR-mediated glucose uptake at 2 h, which indicates that neither transcription nor translation is involved in GPCR stimulated glucose uptake.

To exemplify that GPCRs stimulate GLUT translocation L6 cells and human primary skeletal muscle cells (SKMC) were purchased from Karocell AB (Stockholm Sweden), Lonza and promocell GmbH (Heidelberg, Germany) and grown in Hams F-10 media containing 20% heat-inactivated FBS, 2 mM L-glutamine, 50 U/ml penicillin and 50 µg/ml streptomycin in a 37° C. incubator with 8% $CO_2$. Differentiation was initiated by reducing FBS levels to 4% for 3 days followed by 2% for 4 days. Prior to each experiment, the SKMC were kept in serum free media over night. Cells were grown in 12-well plates and differentiated for 7 days with cells serum starved overnight on day 6. In the morning of day 7, fresh serum free medium was added 2 h before stimulation with drugs indicated in each experiment. Cells were harvested and run on polyacrylamide gels and electro transferred to Hybond-P PVDF membranes (pore size 0.45 µm; GE Healthcare UK Limited, Buckinghamshire, UK). Primary antibodies GLUT1 (ab652, Abcam, 1:1000 dilution) GLUT4-antibodies (Cell Signaling Technology, Inc., #2299, 1:1000 dilution) were detected using a secondary HRP-linked IgG (anti-rabbit, Cell Signaling Technology, Inc., #7074, 1:2000 dilution) and chemiluminescence (ECL, GE Healthcare). All primary antibodies were diluted in TBS-T with 5% BSA while secondary antibodies were diluted in TBS-T with 5% milk. Quantification of blots was performed by the software MacBiophotonics ImageJ. Cells were grown in 4 well culture chamber slides (BD Biosciences, Franklin Lakes, BJ) and differentiated for 7 days. The cells were serum starved overnight and stimulated with insulin (1 µM) or GPCR agonist isoprenaline (1 µM) for 2 h. Cells were fixed for 5 min with 4% formaldehyde in PBS and quenched with 50 mM glycine in PBS for 10 min. Cells were blocked with 5% BSA in PBS and incubated with GLUT4 primary antibody solution (1:200 dilution in 1.5% BSA in PBS) overnight at 4° C. Cells were washed with PBS and incubated with Alexa Fluor® 488-conjugated goat anti-rabbit IgG or Alexa Fluor®555-conjugated goat anti-rabbit IgG or Alexa Fluor® 488-conjugated rabbit anti-goat IgG secondary antibody (1:500 dilution, 1.5% BSA in PBS) for 1 h. Slides were mounted with ProLong® Gold antifade reagent (Invitrogen). Images were observed in an inverted laser scanning microscope (LSM 510META; Carl Zeiss, Advanced Imaging Microscopy, Jena, Germany). Insulin stimulates glucose uptake by GLUT4 translocation (Thong, Dugani & Klip 2005). Given the evidence that GLUT4 is also involved in GPCR-mediated glucose uptake, this can be examined by immunohistochemistry.

Figure 6A:
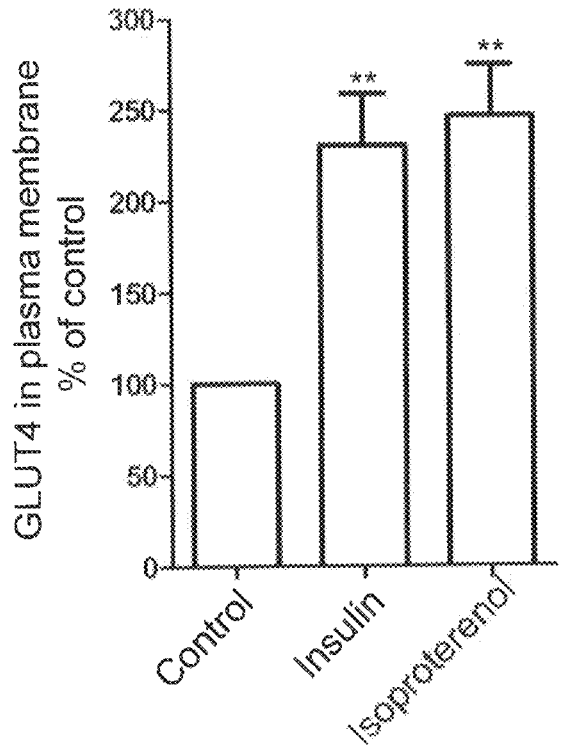
FIGS. 6A and 6B are (6A) a bar chart showing the presence of GLUT4 in plasma membrane (% of control) in L6 myotubes brought into contact with insulin, isoprenaline or, as a control, vehicle only; and (6B) a bar chart showing the presence of GLUT4 in plasma membrane (% of control) in human skeletal muscle cells (SKMC) brought into contact with insulin, isoprenaline or, as a control, vehicle only.
Figure 6B:
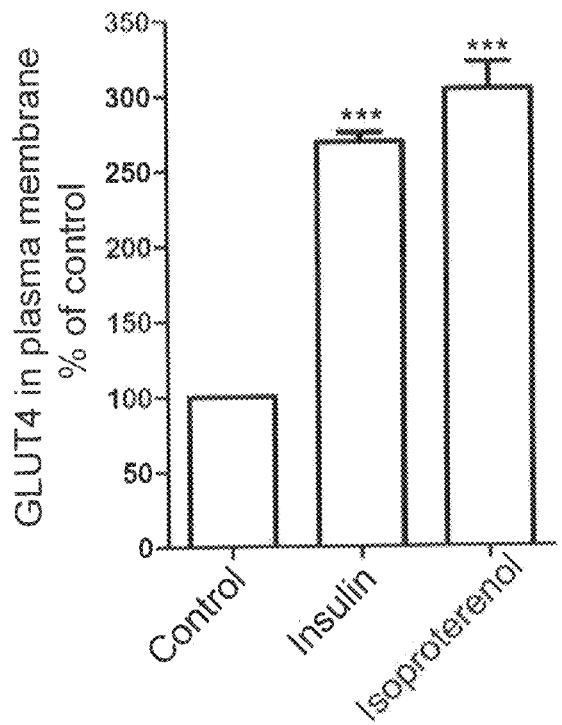

Imaging of non-permeabilized L6 myoblasts showed GLUT4 recruitment to the plasma membrane to the same extent with both isoproterenol and insulin. Robust translocation of GLUT4 to the plasma membrane was observed in L6 cells following GPCR or insulin stimulation. In FIGS. 6A and 6B, which represents quantification of n=3, it is shown that GPCRs stimulate GLUT4 translocation to the plasma membrane in both L6 skeletal muscle cells and human SKMC.

Example 4

GRK2 siRNA constructs (Sigma Aldrich) as well as control sequence was transfected into L6 mytoubes by electroporation. Differentiated L6 cells were detached by washing in PBS followed by 5 minutes of incubation in trypsin/EDTA (0.1% trypsin w/v, 0.02% EDTA w/v). The detached cells were transferred to Eppendorf tubes and centrifugation at 1000×g for 3 minutes was performed before supernatant was removed and the cells were resuspended in 20 µl/well of SE Cell Line Nucleofector® (Lonza) and 100 nM siRNA. Cells were transferred to a 16-well microcuvette plate (Lonza) and were electroporated in a 4D-Nucleofector® (Lonza). 80 µl of pre-warmed RPMI1640 medium were added to the each microcuvette well for 5 min before the cells were transferred to the Eppendorf tubes containing culture media. Cells were serum starved over night and glucose uptake measured 24 hours after transfection.

Figure 7:
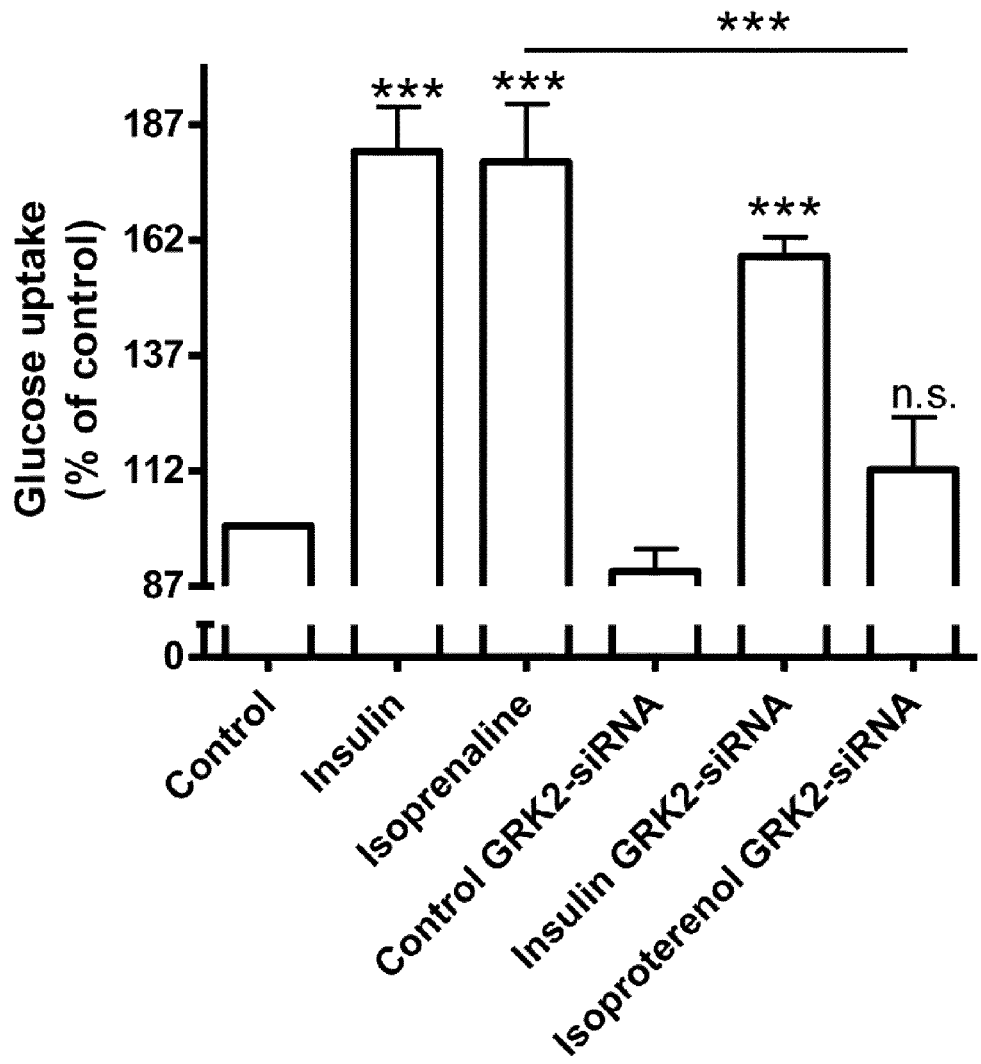
FIG. 7 is a bar chart showing glucose uptake (% of control) in L6 myotubes brought into contact with insulin, isoprenaline or, as a control, vehicle only, with or without transfection with GRK2-siRNA.

GRK2 is known to phosphorylate the intracellular domain of the activated GPCRs and has been implicated in several events such as desensitization, receptor internalization, β-arrestin binding and negative regulation of Erk-phosphorylation (Nobles et al. 2011, Violin, Ren & Lefkowitz 2006). GRK2 is also known to regulate GPCR trafficking in a phosphorylation-independent manner through direct protein-protein interactions (Evron, Daigle & Caron 2012b). Emerging evidence suggests that GRK2 can act as a key and integrative node in a very complex network of functional interactions by phosphorylating non-receptor substrate or by interacting directly with signaling molecules. However, very little is known about the role of GRK2 in skeletal muscle cells and this is the first time that it is shown to be the key molecule in GPCR triggered glucose uptake in skeletal muscle. Thus, FIG. 7 shows that GPCR stimulated glucose uptake is inhibited by GRK2 down-regulation in L6 skeletal muscle cells.

Example 5

Human prostate carcinoma (22rv1) cells were grown for 7 days in RPMI-1640 medium. Human prostate tissue, its cancers and cells derived from those cancers have been shown to express and depend heavily on GLUT1 and to a lesser degree on GLUT2, GLUT7, GLUT9, GLUT11 and GLUT12, but not to express GLUT4 or express GLUT4 at a very low level. This indicates that glucose uptake depends on GLUT1 and not GLUT4 in these cells (Macheda, Rogers & Best 2005, Reinicke et al. 2012, Chandler et al. 2003).

At day 7, 22rv1 cells were treated with siRNA. siRNA constructs GRK2 (Sigma Aldrich) as well as control sequence were transfected into 22rv1 cells by lipofectamine (Life Technologies Corp.) according to the manufacturer's protocol. Cells were serum starved over night and glucose uptake was measured 24 hours after transfection. Cells were stimulated with drugs for totally 2 h, unless otherwise stated.

Figure 8:
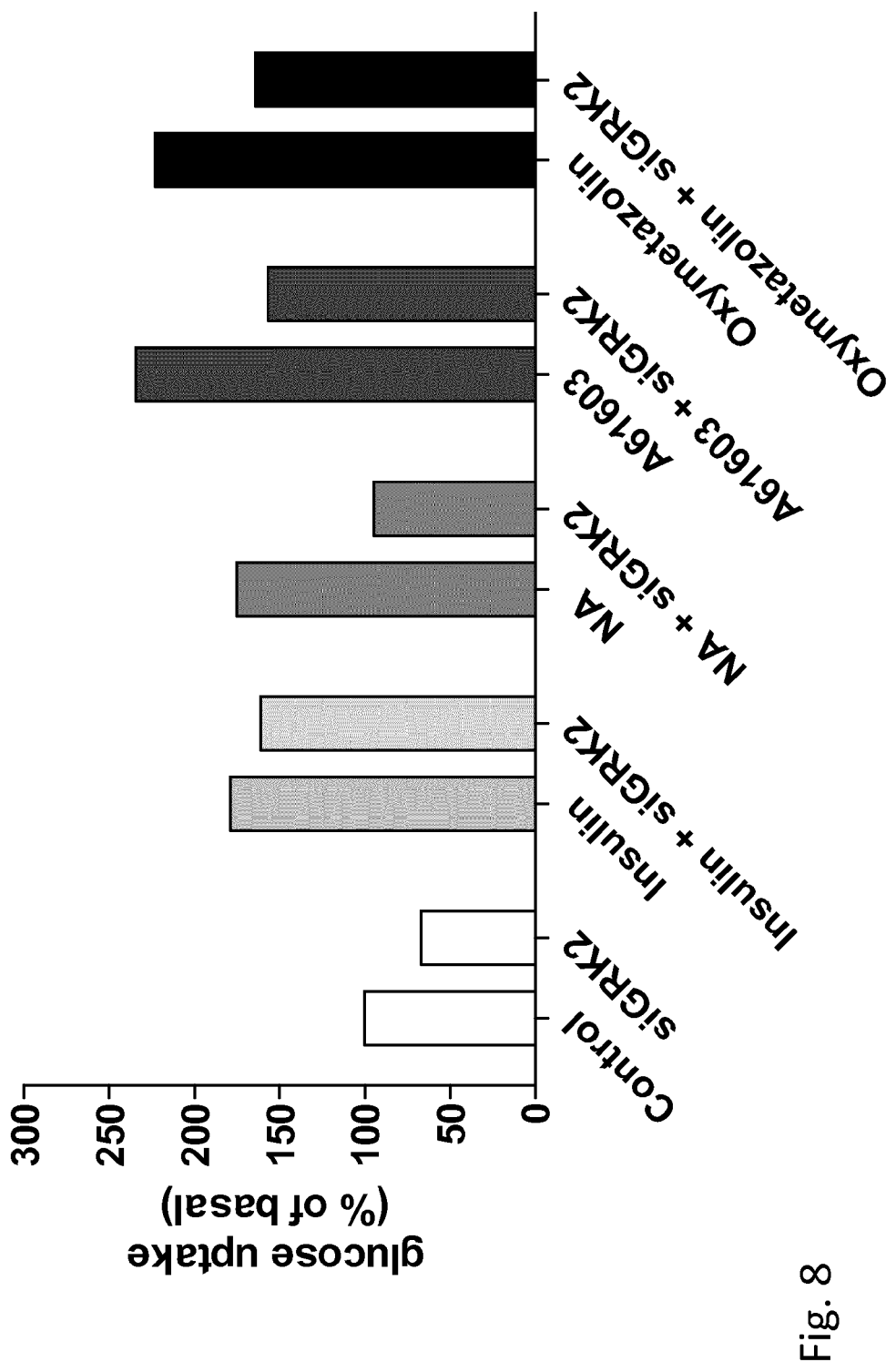
FIG. 8 is a bar chart showing glucose uptake (% of control) in human prostate cancer cells (22rv1 cells) brought into contact with insulin, noradrenaline (NA), A61603, oxymetazoline or, as a control, vehicle only, with or without transfection with GRK2-siRNA.

GRK2 down-regulation with siRNA inhibited glucose uptake stimulated by the GPCR agonists norepinephrine (NA) (agonist for all adrenergic receptors), A61603 (selective for alpha1-adrenergic receptors) and oxymetazoline (agonist for both alpha1- and alpha2-adrenergic receptors) (FIG. 8). The different GPCR classes of alpha adrenergic receptors (6 different isoforms) that are stimulated do not increase the classical secondary messenger cAMP and it is clear that GPCRs agonists in different classes used herein increase glucose uptake and are also inhibited by down-regulation of GRK. This shows that cells that depend on other GLUTs than GLUT4 can be used in the screening method of the invention. It also exemplifies that a large number of GPCRs (coupled to different classical secondary messengers) stimulate glucose uptake through GRK.

Example 6

Glucose uptake was detected by $^3$H-2-dexoy-glucose as previously described (Nevzorova 2002), with minor modifications. Differentiated L6-myotubes were serum-starved over night in media containing 0.5% fatty-acid free BSA and stimulated with agonists for totally 2 h, unless otherwise stated. Cells were exposed to 50 nM $^3$H-2-dexoy-glucose in glucose free media for 6-10 minutes before the experiment was ended by washing the cells in ice-cold PBS or glucose free media. Cells were lysed in 0.2 M NaOH for 1 h in 60° C., mixed with scintillation buffer (Emulsifier Safe, Perkin Elmer) and radioactivity detected in a β-counter (Tri-Carb 2800TR, Perkin Elmer).

PCR measurements showed L6-cells, mytotubes as well as myoblasts, to express the GRK isoforms GRK2, GRK4, GRK5 and GRK6, but not GRK3 (not shown). Previous studies of GRK proteins in rat muscles have revealed that only GRK2 and GKR5 are expressed in this tissue (Jones, Baker & Greenhaff 2003). This information makes it possible to examine the possible role for GRKs in BRL37344-mediated glucose uptake.

Figure 9A:
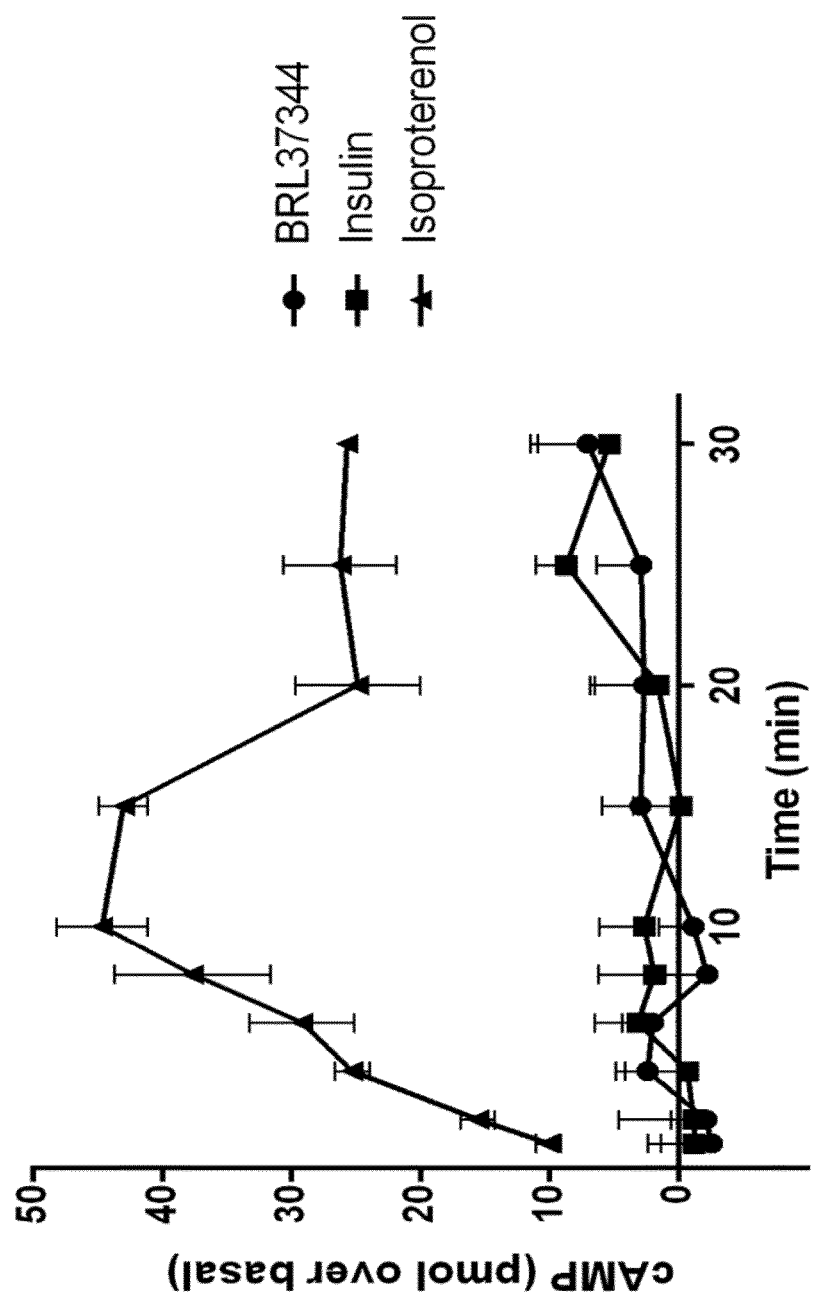
FIGS. 9A and 9B are (9A) a graph showing the presence of the classical secondary messenger cAMP (pmol over basal) plotted against time (min) in L6 myotubes brought into contact with the GPCR agonist BR37344, isoproterenol or insulin; and (9B) a bar chart showing glucose uptake (% of control) in L6 myotubes brought into contact with BR37344, isoproterenol, insulin or, as a control, vehicle only; with or without transfection with GRK2 siRNA.
Figure 9B:
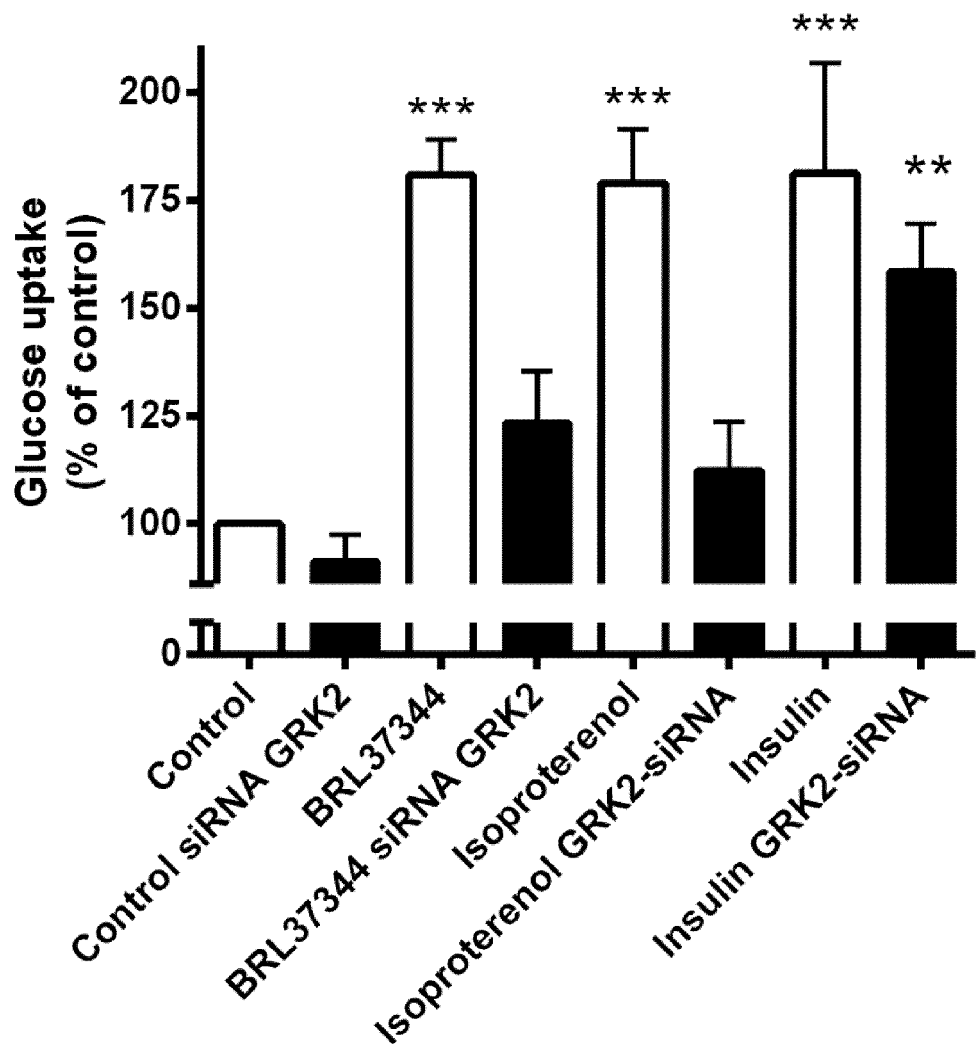

Stimulation with the beta adrenergic agonist BRL 37344 ((±)-(R*,R*)-[4-[2-[[2-(3-chlorophenyl)-2-hydroxy-ethyl]amino]propyl]phenoxy]acetic acid) did not significantly increase the contents of the classical and most studied secondary messenger cAMP over basal in skeletal muscle cells. At no time point examined did this GPCR agonist increase the presence of classical secondary messenger cAMP (FIG. 9A). Knocking down GRK2 with siRNA significantly inhibited beta-adrenergic (BRL37344)-mediated glucose uptake showing that GRK2 is mediating the GPCR signal but that this is not through the classical secondary messenger cAMP. Also the effect of isoproterenol (another beta-adrenergic agonist) was significantly diminished, while the effect of insulin could not be blocked, indicating the effect to be specific. Thus the beta-adrenergic (a prototypical example of a GPCR) agonist BRL 37344 stimulate glucose uptake, but this is not via the classical secondary messenger cAMP, but via GRK2 as illustrated in FIG. 9B.

This exemplifies that GPCRs can stimulate glucose uptake via GRK in peripheral tissues without stimulating classical secondary messengers such as cAMP.

The above examples further illustrate that the screening method according to the invention allows for the identification of a compound useful for the treatment of a condition involving a dysregulation of glucose homeostasis or glucose uptake in a mammal.

Example 7

The above described experiments together also illustrate the screening method of the invention. Thus in Example 6, bringing cells expressing GRK2 into contact with the "screened compound" BRL37344 elicited a glucose uptake, expressed in % of the glucose uptake of the same cells brought into contact with vehicle only, of 175% (FIG. 9B). Under the same conditions, BRL37344 caused a glucose uptake that is only 125%. This indicates that BRL37344 causes a response of the GRK in the cells expressing GRK.

As a comparison, the glucose uptake caused by isoproterenol in (untransfected) cells expressing GRK was about 175% and 120% in transfected cells not expressing GRK. This indicates that isoproterenol too causes a response of the GRK in the cells expressing GRK.

Further, to determine whether contacting BRL37344 causes a response of a classical secondary messenger in cells with which it is brought into contact, the concentration of cAMP was measured during a period of time. As a reference, cAMP in cells not brought into contact was measured. In FIG. 9A the difference $\Delta_1$ for BRL37344 is plotted, and the maximum difference is about 8 pmol. The corresponding difference for isoproterenol, is about 45 pmol. The calculated value of r" therefore is 8/45=0.18.

While this invention has been described with respect to various specific examples it is to be understood that the invention is not limited by this and it can be variously practiced within the scope of the claims.

REFERENCE LIST

Barnes, K., Ingram, J. C., Porras, O. H., Barros, L. F., Hudson, E. R., Fryer, L. G., Foufelle, F., Carling, D., Hardie, D. G. & Baldwin, S. A. 2002, "Activation of GLUT1 by metabolic and osmotic stress: potential involvement of AMP-activated protein kinase (AMPK)", Journal of cell science, vol. 115, no. Pt 11, pp. 2433-2442.

Carayannopoulos, M. O., Chi, M. M., Cui, Y., Pingsterhaus, J. M., McKnight, R. A., Mueckler, M., Devaskar, S. U. & Moley, K. H. 2000, "GLUT8 is a glucose transporter responsible for insulin-stimulated glucose uptake in the blastocyst", Proceedings of the National Academy of Sciences of the United States of America, vol. 97, no. 13, pp. 7313-7318.

Chandler, J. D., Williams, E. D., Slavin, J. L., Best, J. D. & Rogers, S. 2003, "Expression and localization of GLUT1 and GLUT12 in prostate carcinoma", Cancer, vol. 97, no. 8, pp. 2035-2042.

DeFronzo, R. A., Ferrannini, E., Sato, Y., Felig, P. & Wahren, J. 1981, "Synergistic interaction between exercise and insulin on peripheral glucose uptake", The Journal of clinical investigation, vol. 68, no. 6, pp. 1468-1474.

Dehvari, N., Hutchinson, D. S., Nevzorova, J., Dallner, O. S., Sato, M., Kocan, M., Merlin, J., Evans, B. A., Summers, R. J. & Bengtsson, T. 2011, "beta(2)-Adrenoceptors increase translocation of GLUT4 via G protein-coupled receptor kinase sites in the receptor C-terminal tail", British journal of pharmacology.

Drake, M. T., Shenoy, S. K. & Lefkowitz, R. J. 2006, "Trafficking of G protein-coupled receptors", Circulation research, vol. 99, no. 6, pp. 570-582.

Evron, T., Daigle, T. L. & Caron, M. G. 2012a, "GRK2: multiple roles beyond G protein-coupled receptor desensitization", Trends in pharmacological sciences, vol. 33, no. 3, pp. 154-164.

Evron, T., Daigle, T. L. & Caron, M. G. 2012b, "GRK2: multiple roles beyond G protein-coupled receptor desensitization", Trends in pharmacological sciences, vol. 33, no. 3, pp. 154-164.

Gawlik, V., Schmidt, S., Scheepers, A., Wennemuth, G., Augustin, R., Aumuller, G., Moser, M., Al-Hasani, H., Kluge, R., Joost, H. G. & Schurmann, A. 2008, "Targeted disruption of Slc2a8 (GLUT8) reduces motility and mitochondrial potential of spermatozoa", Molecular membrane biology, vol. 25, no. 3, pp. 224-235.

Gilman, A. G. 1987, "G proteins: transducers of receptor-generated signals", Annual Review of Biochemistry, vol. 56, pp. 615-649.

Gusovsky, F. 2001, "Measurement of secondary messengers in signal transduction: cAMP and inositol phosphates", Current protocols in neuroscience/editorial board, Jacqueline N. Crawley . . . [et al], vol. Chapter 7, pp. Unit7.12.

Harrison, S. A., Clancy, B. M., Pessino, A. & Czech, M. P. 1992, "Activation of cell surface glucose transporters measured by photoaffinity labeling of insulin-sensitive 3T3-L1 adipocytes", Journal of Biological Chemistry, vol. 267, no. 6, pp. 3783-3788.

Hebert, D. N. & Carruthers, A. 1986, "Direct evidence for ATP modulation of sugar transport in human erythrocyte ghosts", The Journal of biological chemistry, vol. 261, no. 22, pp. 10093-10099.

Hutchinson, D. S. & Bengtsson, T. 2005, "alpha1A-adrenoceptors activate glucose uptake in L6 muscle cells through a phospholipase C-, phosphatidylinositol-3 kinase-, and atypical protein kinase C-dependent pathway", Endocrinology, vol. 146, no. 2, pp. 901-912.

Jones, S. W., Baker, D. J. & Greenhaff, P. L. 2003, "G protein-coupled receptor kinases 2 and 5 are differentially expressed in rat skeletal muscle and remain unchanged following beta2-agonist administration", Experimental physiology, vol. 88, no. 2, pp. 277-284.

Koshy, S., Alizadeh, P., Timchenko, L. T. & Beeton, C. 2010, "Quantitative measurement of GLUT4 translocation to the plasma membrane by flow cytometry", Journal of visualized experiments: JoVE, vol. (45). pii: 2429. doi, no. 45, pp. 10.3791/2429.

Liggett, S. B., Shah, S. D. & Cryer, P. E. 1988, "Characterization of beta-adrenergic receptors of human skeletal muscle obtained by needle biopsy", The American Journal of Physiology, vol. 254, no. 6 Pt 1, pp. E795-8.

Macheda, M. L., Rogers, S. & Best, J. D. 2005, "Molecular and cellular regulation of glucose transporter (GLUT) proteins in cancer", Journal of cellular physiology, vol. 202, no. 3, pp. 654-662.

Murata, H., Hruz, P. W. & Mueckler, M. 2002, "Indinavir inhibits the glucose transporter isoform Glut4 at physiologic concentrations", AIDS (London, England), vol. 16, no. 6, pp. 859-863.

Nevzorova, J., Bengtsson, T., Evans, B. A. & Summers, R. J. 2002, "Characterization of the beta-adrenoceptor subtype involved in mediation of glucose transport in L6 cells", British journal of pharmacology, vol. 137, no. 1, pp. 9-18.

Nevzorova, J., Evans, B. A., Bengtsson, T. & Summers, R. J. 2006, "Multiple signalling pathways involved in beta2- adrenoceptor-mediated glucose uptake in rat skeletal muscle cells", *British journal of pharmacology*, vol. 147, no. 4, pp. 446-454.

Nobles, K. N., Xiao, K., Ahn, S., Shukla, A. K., Lam, C. M., Rajagopal, S., Strachan, R. T., Huang, T. Y., Bressler, E. A., Hara, M. R., Shenoy, S. K., Gygi, S. P. & Lefkowitz, R. J. 2011, "Distinct phosphorylation sites on the beta(2)-adrenergic receptor establish a barcode that encodes differential functions of beta-arrestin", *Science signaling*, vol. 4, no. 185, pp. ra51.

Palmada, M., Boehmer, C., Akel, A., Rajamanickam, J., Jeyaraj, S., Keller, K. & Lang, F. 2006, "SGK1 kinase upregulates GLUT1 activity and plasma membrane expression", *Diabetes*, vol. 55, no. 2, pp. 421-427.

Ploug, T., Galbo, H., Vinten, J., Jorgensen, M. & Richter, E. A. 1987, "Kinetics of glucose transport in rat muscle: effects of insulin and contractions", *The American Journal of Physiology*, vol. 253, no. 1 Pt 1, pp. E12-20.

Reinicke, K., Sotomayor, P., Cisterna, P., Delgado, C., Nualart, F. & Godoy, A. 2012, "Cellular distribution of Glut-1 and Glut-5 in benign and malignant human prostate tissue", *Journal of cellular biochemistry*, vol. 113, no. 2, pp. 553-562.

Rodnick, K. J., Piper, R. C., Slot, J. W. & James, D. E. 1992, "Interaction of insulin and exercise on glucose transport in muscle", *Diabetes care*, vol. 15, no. 11, pp. 1679-1689.

Santulli, G. & Iaccarino, G. 2013, "Pinpointing beta adrenergic receptor in ageing pathophysiology: victim or executioner? Evidence from crime scenes", *Immunity & ageing: I & A*, vol. 10, no. 1, pp. 10-4933-10-10.

Sarabia, V., Ramlal, T. & Klip, A. 1990, "Glucose uptake in human and animal muscle cells in culture", *Biochemistry and cell biology=Biochimie et biologie cellulaire*, vol. 68, no. 2, pp. 536-542.

Shah, K., Desilva, S. & Abbruscato, T. 2012, "The Role of Glucose Transporters in Brain Disease: Diabetes and Alzheimer's Disease", *International journal of molecular sciences*, vol. 13, no. 10, pp. 12629-12655.

Simpson, I. A., Dwyer, D., Malide, D., Moley, K. H., Travis, A. & Vannucci, S. J. 2008, "The facilitative glucose transporter GLUT3: 20 years of distinction", *American journal of physiology. Endocrinology and metabolism*, vol. 295, no. 2, pp. E242-53.

Sobel, M. E., Wolfson, E. B. & Krulwich, T. A. 1973, "Abolition of cryticity of *Arthrobacter* pyridinolis toward glucose and alpha-glucosides by tricarboxylic acid cycle intermediates", *Journal of Bacteriology*, vol. 116, no. 1, pp. 271-278.

Taha, C., Mitsumoto, Y., Liu, Z., Skolnik, E. Y. & Klip, A. 1995, "The insulin-dependent biosynthesis of GLUT1 and GLUT3 glucose transporters in L6 muscle cells is mediated by distinct pathways. Roles of p21ras and pp70 S6 kinase", *The Journal of biological chemistry*, vol. 270, no. 42, pp. 24678-24681.

Taverna, R. D. & Langdon, R. G. 1973, "Reversible association of cytochalasin B with the human erythrocyte membrane. Inhibition of glucose transport and the stoichiometry of cytochalasin binding", *Biochimica et biophysica acta*, vol. 323, no. 2, pp. 207-219.

Thong, F. S., Dugani, C. B. & Klip, A. 2005, "Turning signals on and off: GLUT4 traffic in the insulin-signaling highway", *Physiology* (Bethesda, Md.), vol. 20, pp. 271-284.

Violin, J. D., Ren, X. R. & Lefkowitz, R. J. 2006, "G-protein-coupled receptor kinase specificity for beta-arrestin recruitment to the beta2-adrenergic receptor revealed by fluorescence resonance energy transfer", *The Journal of biological chemistry*, vol. 281, no. 29, pp. 20577-20588.

Watson-Wright, W. M. & Wilkinson, M. 1986, "The muscle slice—a new preparation for the characterization of beta-adrenergic binding in fast- and slow-twitch skeletal muscle", *Muscle & nerve*, vol. 9, no. 5, pp. 416-422.

Zierath, J. R. 1995, "In vitro studies of human skeletal muscle: hormonal and metabolic regulation of glucose transport", *Acta physiologica Scandinavica.Supplementum*, vol. 626, pp. 1-96.

The invention claimed is:

1. A method of screening for a candidate compound for the treatment of diabetes in a mammal, said method comprising:
    bringing a compound into contact with cells that express an adrenergic receptor and that further express G protein coupled receptor kinase 2 (GRK2);
    determining whether the contacting causes a response of GRK2 in the cells brought into contact with the compound;
    determining whether the contacting causes a response of cAMP in the cells brought into contact with the compound; and
    selecting the compound as a candidate compound, if the compound causes an increase of GRK2 activity but does not cause a response of cAMP in the cells, and
    testing the candidate compound in pharmacological, clinical and/or toxicological tests.

2. The method of claim 1, wherein the compound is identified as a candidate compound by comparing the determined GRK2 activity and response of cAMP, with activity of the GRK2 and response of cAMP determined in cells that have not been brought into contact with the compound.

3. The method of claim 1, comprising bringing the compound into contact with cells that express an adrenergic receptor and that further express a GRK2 and a glucose transporter (GLUT).

4. The method of claim 3, wherein the GLUT is GLUT4.

5. The method of claim 3, comprising determining a response of a GLUT in the cells brought into contact with the compound; selecting the compound as a candidate compound, if the compound causes a GLUT response; and testing the candidate compound in pharmacological, clinical and/or toxicological tests.

6. The method of claim 5, wherein determining a response of the GLUT comprises detecting translocation of the GLUT to the cell membrane of the cells.

7. The method of claim 5, wherein determining a response of a GLUT comprises measuring uptake of a hexose in the cells brought into contact with the compound.

8. The method of claim 7, wherein the hexose is glucose.

9. The method of claim 5, wherein the candidate compound is further identified by comparing a determined GLUT response with the GLUT response determined in cells that have not been brought into contact with the compound.

10. The method of claim 1, wherein the cells are mammalian cells.

11. The method of claim 10, wherein the mammalian cells are muscle cells.

* * * * *